US012584140B2

(12) United States Patent
Bundock

(10) Patent No.: US 12,584,140 B2
(45) Date of Patent: Mar. 24, 2026

(54) TYPE V CRISPR/NUCLEASE-SYSTEM FOR GENOME EDITING IN PLANT CELLS

(71) Applicant: Keygene N.V., Wageningen (NL)

(72) Inventor: Paul Bundock, AE Wageningen (NL)

(73) Assignee: KEYGENE N.V., Wageningen (NL)

(*) Notice: Subject to any disclaimer, the term of this patent is extended or adjusted under 35 U.S.C. 154(b) by 1059 days.

(21) Appl. No.: 17/259,359

(22) PCT Filed: Jul. 12, 2019

(86) PCT No.: PCT/EP2019/068839
§ 371 (c)(1),
(2) Date: Jan. 11, 2021

(87) PCT Pub. No.: WO2020/011985
PCT Pub. Date: Jan. 16, 2020

(65) Prior Publication Data
US 2021/0238612 A1    Aug. 5, 2021

Related U.S. Application Data

(60) Provisional application No. 62/697,021, filed on Jul. 12, 2018.

(30) Foreign Application Priority Data

Sep. 12, 2018    (EP) .................................... 18194078

(51) Int. Cl.
*C12N 15/82*    (2006.01)
*C12N 9/22*    (2006.01)

(52) U.S. Cl.
CPC ........... *C12N 15/8202* (2013.01); *C12N 9/22* (2013.01); *C12Y 301/00* (2013.01)

(58) Field of Classification Search
USPC ........................................................ 435/468
See application file for complete search history.

(56) References Cited

U.S. PATENT DOCUMENTS

| | | | | |
|---|---|---|---|---|
| 9,982,279 B1 * | 5/2018 | Gill | ........................ | C12N 15/85 |
| 10,017,760 B2 * | 7/2018 | Gill | ........................ | C12N 15/11 |
| 2020/0131536 A1 * | 4/2020 | Kim | ........................ | C12N 9/78 |

FOREIGN PATENT DOCUMENTS

| | | | | |
|---|---|---|---|---|
| WO | 2017223538 | 12/2017 | | |
| WO | 2018071672 | 4/2018 | | |
| WO | WO-2018071672 A1 * | 4/2018 | ......... | C12N 15/1072 |

OTHER PUBLICATIONS

Woo, J., Kim, J., Kwon, S. et al. DNA-free genome editing in plants with preassembled CRISPR-Cas9 ribonucleoproteins. Nat Biotechnol 33, 1162-1164 (2015). https://doi.org/10.1038/nbt.3389 (Year: 2015).*
Gamborg, O. L., J. P. Shyluk, and E. A. Shahin. "Isolation, fusion and culture of plant protoplasts." Plant tissue culture: methods and applications in agriculture (1981): 115-153. (Year: 1981).*
Li, X., Wang, Y., Liu, Y et al. Base editing with a Cpf1-cytidine deaminase fusion. Nat Biotechnol 36, 324-327 (2018). https://doi.org/10.1038/nbt.4102 (Year: 2018).*
Lee, Kunwoo, et al. "Synthetically modified guide RNA and donor DNA are a versatile platform for CRISPR-Cas9 engineering." elife 6 (2017): e25312. (Year: 2017).*
Renaud, Jean-Baptiste, et al. "Improved genome editing efficiency and flexibility using modified oligonucleotides with TALEN and CRISPR-Cas9 nucleases." Cell reports 14.9 (2016): 2263-2272 (Year: 2016).*
Gamborg, Oluf L., and J. P. Shyluk. "Nutrition, media and characteristics of plant cell and tissue cultures." Plant tissue culture: methods and applications in agriculture (1981): 21-44. See p. 30 (Year: 1981).*
Lin, Choun-Sea, et al. "Application of protoplast technology to CRISPR/Cas9 mutagenesis: from single-cell mutation detection to mutant plant regeneration." Plant biotechnology journal 16.7 (2018): 1295-1310. (Year: 2018).*
International Search Report mailed Sep. 9, 2019 in connection with PCT/US19/068839.
Written Opinion mailed Sep. 9, 2019 in connection with PCT/US19/068839.
Zaidi Syed Shan-E-Ali et al., "CRISP-Cpf1: A new tool for plant genome Editing" Trends in Plant Science, vol. 22, No. 7, Jul. 1, 2017, pp. 550-553.
Malzahn Aimee et al., "Plant genome editing with TALEN and CRISP" Cell & Bioscience, Biomed Central LTD, London, UK, vol. 7, Apr. 24, 2017, pp. 1-18.
Observations by Third Party filed Jan. 24, 2025 in connection with EP No. 19740353.8.

(Continued)

*Primary Examiner* — Amjad Abraham
*Assistant Examiner* — Kelsey L McWilliams
(74) *Attorney, Agent, or Firm* — Troutman Pepper Locke LLP

(57) ABSTRACT

Provided is a method for targeted modification of DNA in a plant cell using crRNA-guided MAD7-nuclease and compositions and kits for doing the same. Preferably, the MAD7-nuclease comprises two catalytically active endonuclease domains or comprises at least one catalytically inactive endonuclease domain. Furthermore, the MAD7-endonuclease may be fused to a functional domain, such as a deaminase domain.

13 Claims, 1 Drawing Sheet

Specification includes a Sequence Listing.

(56)  References Cited

OTHER PUBLICATIONS

Erik Jongedijk, Genome Editing in Agriculture, An Industry Perspective On Requirements For Robust Outcomes Beyond Low Hanging Fruits, given in the 6th Plant Genomics & gene Editing Congress, The Netherlands 14th and 15th of May of 2018, pp. 1-17.

Hyeran Kim et al., "CRISPR/Cpf1-mediated DNA-free plant genome editing", Nature Communications, 8:14406, 2017, pp. 1-7, DOI: 10.1038/ncomms14406.

Yingxiao Zhang et al. "Expanding the scope of plant genome engineering with Cas12a orthologs and highly multiplexable editing systems", Nature Communications, 2021, 12:1944, pp. 1-11, https://doi.org/10.1038/s41467-021-22330-w.

* cited by examiner

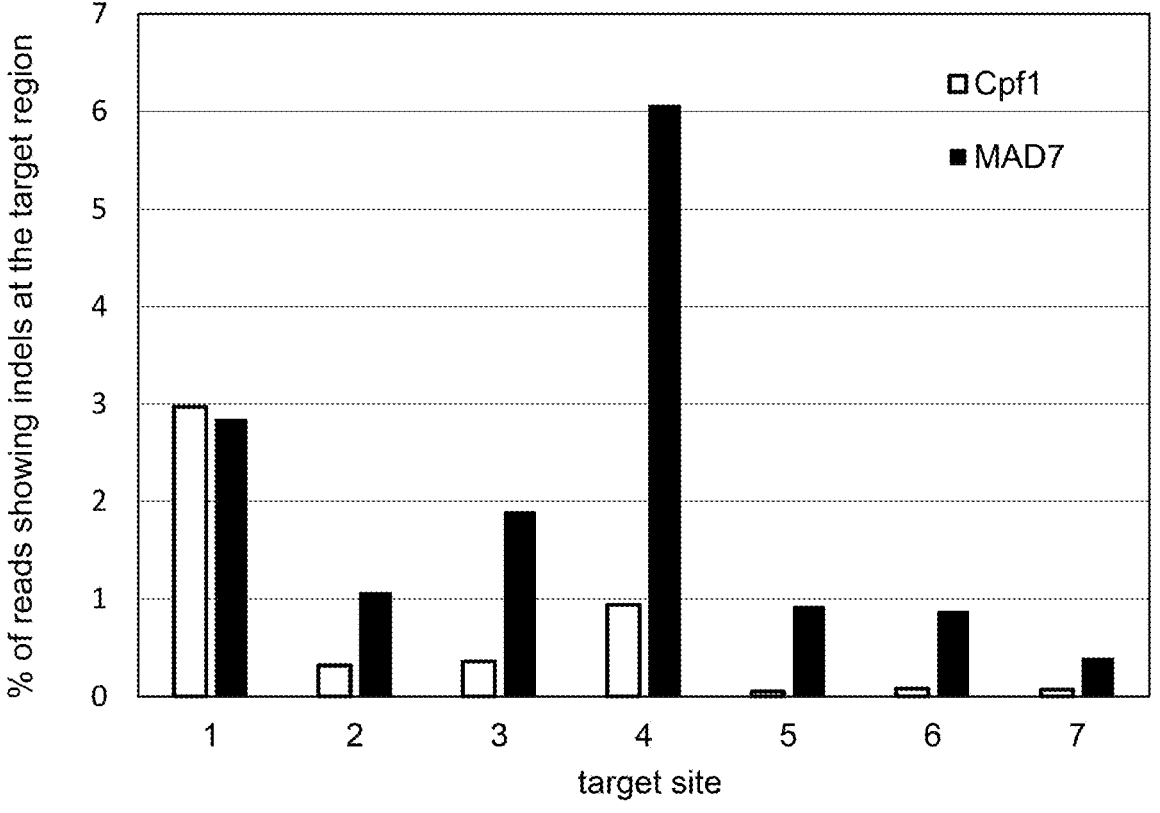

TYPE V CRISPR/NUCLEASE-SYSTEM FOR GENOME EDITING IN PLANT CELLS

CROSS-REFERENCE TO RELATED APPLICATIONS

This application is a 371 National Stage of PCT/EP19/068839, filed Jul. 12, 2019, which claims priority to U.S. Provisional Patent Application No. 62/697,021, filed Jul. 12, 2018 and EP 18194078.4, filed Sep. 12, 2018, which are hereby incorporated by reference in their entirety.

FIELD OF THE INVENTION

The present invention is in the field of molecular biology and plant biology. The invention concerns targeted DNA modifications, including methods and compositions for making such modifications.

SEQUENCE LISTING

The instant application contains a Sequence Listing which has been submitted electronically in ASCII format and is hereby incorporated by reference in its entirety. Said ASCII copy, created on Nov. 16, 2023, is named "REPLACEMENT_SL_11162023.txt" and is 77,411 bytes in size.

BACKGROUND

The process of deliberately creating changes in the genetic material of living cells has the goal of modifying one or more genetically encoded biological properties of that cell, or of the organism of which the cell forms part or into which it can regenerate. These changes can e.g. take the form of deletion of parts of the genetic material, addition of exogenous genetic material, or changes in the existing nucleotide sequence of the genetic material. Methods of altering the genetic material of eukaryotic organisms have been known for over 20 years, and have found widespread application in plant, human and animal cells and micro-organisms for improvements in the fields of agriculture, human health, food quality and environmental protection. The most common methods consist of adding exogenous DNA fragments to the genome of a cell, which will then confer a new property to that cell or its organism over and above the properties encoded by already existing genes, including applications in which the expression of existing genes will thereby be suppressed. Although many such examples are effective in obtaining the desired properties, these methods have several drawbacks. For example, these conventional methods are not very precise, because there is not always control over the genomic positions in which the exogenous DNA fragments are inserted (and hence over the ultimate levels of expression), and the desired effect will have to manifest itself over the natural properties encoded by the original and well-balanced genome. On the contrary, methods of genome editing that will result in the addition, deletion or conversion of nucleotides in predefined genomic loci will allow the precise modification of existing genes.

By using site-specific nucleases, such as zinc finger nucleases (ZFNs), transcription activator like effector nucleases (TALENs), and Clustered Regularly Interspaced Short Palindromic Repeat (CRISPR) nucleases, the field of targeted DNA alteration is rapidly developing.

CRISPRs (Clustered Regularly Interspaced Short Palindromic Repeats) are loci containing multiple short direct repeats and are found in 40% of the sequenced bacteria and 90% of the sequenced archaea. The CRISPR repeats form a system of acquired bacterial immunity against genetic pathogens such as bacteriophages and plasmids. When a bacterium is challenged with a pathogen, a small piece of the pathogen's genome is processed by CRISPR associated proteins (Cas) and incorporated into the bacterial genome between CRISPR repeats. The CRISPR loci are then transcribed and processed to form so called crRNAs which include approximately 30 bps of sequence identical to the pathogen's genome. These RNA molecules form the basis for the recognition of the pathogen upon a subsequent infection and lead to silencing of the pathogen genetic elements through direct digestion of the pathogen's genome. The Cas9 protein is an essential component of the type-II CRISPR/Cas system from S. pyogenes and forms an endonuclease, when combined with the crRNA and a second RNA termed the trans-activating crRNA (tracrRNA), which targets the invading pathogenic DNA for degradation by the introduction of DNA double strand breaks (DSBs) at the position in the genome defined by the crRNA. This type-II CRISPR/Cas9 system has been proven to be a convenient and effective tool in biochemistry that, via the targeted introduction of double-strand breaks and the subsequent activation of endogenous repair mechanisms, is capable of introducing modification in eukaryotic genomes at sites of interest. Jinek et al. (2012, Science 337: 816-820) demonstrated that a single chain chimeric RNA (single guide RNA, sRNA, sgRNA), produced by combining the essential sequences of the crRNA and tracrRNA into a single RNA molecule, was able to form a functional endonuclease in combination with Cas9. Many different CRISPR/Cas systems have been identified from different bacterial species (Zetsche et al. 2015 Cell 163, 759-771; Kim et al. 2017, Nat. Commun. 8, 1-7; Ran et al. 2015. Nature 520, 186-191).

The CRISPR/Cas9 system can be used for genome editing in a wide range of different organisms and cell types. First a genomic sequence is identified at which the CRISPR/Cas endonuclease should induce a DSB and this is then screened for the presence of a protospacer adjacent motif (PAM). The PAM sequence is essential for the CRISPR/Cas endonuclease activity, is relatively short, and is therefore usually present multiple times in any given sequence of some length. For instance the PAM motif of the S. pyogenes Cas9 protein is NGG, which ensures that for any given genomic sequence multiple PAM motifs are present and so many different guide RNAs can be designed. In addition, guide RNAs can also be designed to target the opposite strands of the same double strand sequence. The sequence immediately adjacent to the PAM is incorporated into the guide RNA. This can differ in length depending upon the CRISPR/Cas system being used. For instance, the optimal length for the targeting sequence in the Cas9 sgRNA is 20nt, and in most cases a sequence of this length is unique in a plant genome. For expression in plant cells a gene coding for a guide RNA can be linked to an RNA polymerase-III promoter, such as the U6 promoter from Arabidopsis, or the corresponding or functionally similar pol-III promoter from the cell type, organism, plant species or family in which the experiments are being performed.

The CRISPR/Cas endonuclease can be expressed in the cell from any form of constitutive or inducible promoter that is suitable for the organism or cell type in which the experiments are being performed. In some instances, the protein expression levels of the CRISPR/Cas endonuclease can be improved by optimization of its codon usage for the specific cell type or organism.

The two components of the CRISPR/Cas system, the endonuclease and the guide RNA(s) can be expressed in the cell from ectopic genomic elements such as (non-replicating) plasmid constructs, viral vectors or introduced directly in the cells or organism as protein (the CRISPR/Cas endonuclease) and RNA (guide RNA). In addition mRNA encoding the CRISPR/Cas endonuclease can be used. When the plasmid or viral vectors are unable to replicate in the transformed cells then the CRISPR/Cas and guide RNA(s) are expressed or present for a short period and then are eliminated from the cell. Stable expression of the CRISPR/Cas protein and guide RNA can be achieved using a transgenic approach whereby the genes coding for them are integrated into the host genome.

Once the CRISPR/Cas endonuclease and the guide RNA is present/expressed in the cell then the complex of the two components scans the genomic DNA for the sequence complementary to the targeting sequence on the guide RNA and adjacent to a PAM sequence. Depending on the CRISPR/Cas endonuclease being used, the complex then induces nicks in both of the DNA strands at varying distances from the PAM. For instance the *S. pyogenes* Cas9 protein introduces nicks in the both DNA strands 3 bps upstream from the PAM sequence to create a blunt DNA DSB.

Once a DNA DSB has been produced the cellular DNA repair machinery, particularly proteins belonging to the non-homologous end joining (NHEJ) pathway, are involved in the re-ligation of the DNA ends. If this DSB is repaired accurately then the sequence again forms a target for cutting by the CRISPR/Cas-guide RNA complex. However, some re-ligation events are imprecise and can lead to the random loss or gain of a few nucleotides at the break, resulting in an indel mutation in the genomic DNA. This results in an alteration of the target sequence that prevents binding of the guide RNA and thus any further DSB induction.

Recently, a second CRISPR/Cas system capable of the programmed introductions of DSBs was characterized, i.e. type-V CRISPR/Cpf1 (also known as CRISPR/Cas12a). The main differences between Cpf1 and Cas9, are that Cpf1 only requires a crRNA instead of both a crRNA and tracrRNA, the optimal spacer of Cpf1 is at least 21 nucleotides and Cpf1 recognizes a T-rich PAM instead of the G-rich PAM of Cas9. Further, the PAM is located upstream of the guide sequence and Cpf1 generates a staggered DSBs distal from the PAM, instead of a blunt-ended DSB proximal to the PAM as generated by Cas9. In WO/2018/115390, which is incorporated herein by reference, effective genome editing in plant cell protoplasts has been demonstrated.

The present inventors now discovered a type-V CRISPR/nuclease system being surprisingly effective in plants cells. Until now, this system, called MAD7, has only been reported to be effective in a prokaryotic host cell (see U.S. Pat. No. 9,982,279, which is incorporated herein by reference).

FIGURE LEGEND

FIG. 1: Comparison of MAD7 and AsCpf1. The percentage of reads showing indels at the target region is shown on the y axis. In each sample either the AsCpf1 (Cpf1) or MAD7 enzyme was expressed together with the appropriate crRNA for targeting the respective target sites as listed in Table 1.

DEFINITIONS

Various terms relating to the methods, compositions, uses and other aspects of the present invention are used throughout the specification and claims. Such terms are to be given their ordinary meaning in the art to which the invention pertains, unless otherwise indicated. Other specifically defined terms are to be construed in a manner consistent with the definition provided herein. Although any methods and materials similar or equivalent to those described herein can be used in the practice for testing of the present invention, the preferred materials and methods are described herein.

It is clear for the skilled person that any methods and materials similar or equivalent to those described herein can be used for practicing the present invention.

Methods of carrying out the conventional techniques used in the methods of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references: Sambrook et al., *Molecular Cloning. A Laboratory Manual*, 2nd Edition, Cold Spring Harbor Laboratory Press, Cold Spring Harbor, N. Y., 1989; Ausubel et al., *Current Protocols in Molecular Biology*, John Wiley & Sons, New York, 1987 and periodic updates; and the series *Methods in Enzymology*, Academic Press, San Diego.

"A," "an," and "the": these singular form terms include plural referents unless the content clearly dictates otherwise. The indefinite article "a" or "an" thus usually means "at least one". Thus, for example, reference to "a cell" includes a combination of two or more cells, and the like.

"About" and "approximately": these terms, when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods. Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

"And/or": The term "and/or" refers to a situation wherein one or more of the stated cases may occur, alone or in combination with at least one of the stated cases, up to with all of the stated cases.

"Comprising": this term is construed as being inclusive and open ended, and not exclusive. Specifically, the term and variations thereof mean the specified features, steps or components are included. These terms are not to be interpreted to exclude the presence of other features, steps or components.

"Exemplary": this terms means "serving as an example, instance, or illustration," and should not be construed as excluding other configurations disclosed herein.

"Plant" refers to either the whole plant or to parts of a plant, such as cells, tissue cultures or organs (e.g. pollen, seeds, ovules, gametes, roots, leaves, flowers, flower buds, branches, anthers, fruit, kernels, ears, cobs, husks, stalks, root tips, grains, embryos, etc.) obtainable from the plant, as well as derivatives of any of these and progeny derived from such a plant by selfing or crossing. Non-limiting examples of plants include crop plants and cultivated plants, such as barley, cabbage, canola, cassava, cauliflower, chicory, cotton, cucumber, eggplant, grape, hot pepper, lettuce, maize, melon, oilseed rape, potato, pumpkin, rice, rye, sorghum, squash, sugar cane, sugar beet, sunflower, sweet pepper, tomato, water melon, wheat, and zucchini.

"Plant cell(s)" include protoplasts, gametes, suspension cultures, microspores, pollen grains, etc., either in isolation or within a tissue, organ or organism. The plant cell can e.g. be part of a multicellular structure, such as a callus, meristem plant organ or an explant.

The terms "construct", "nucleic acid construct", "vector", and "expression vector" are used interchangeably herein and is herein defined as a man-made nucleic acid molecule resulting from the use of recombinant DNA technology. These constructs and vectors therefore do not include naturally occurring nucleic acid molecules although a nucleic acid construct may comprise (parts of) naturally occurring nucleic acid molecules.

The vector backbone may for example be a binary or superbinary vector (see e.g. U.S. Pat. No. 5,591,616, US 2002138879 and WO 95/06722), a co-integrate vector or a T-DNA vector, as known in the art and as described elsewhere herein, into which a chimeric gene is integrated or, if a suitable transcription regulatory sequence is already present, only a desired nucleotide sequence (e.g. a coding sequence, an antisense or an inverted repeat sequence) is integrated downstream of the transcription regulatory sequence. Vectors can comprise further genetic elements to facilitate their use in molecular cloning, such as selectable markers, multiple cloning sites and the like.

The term "gene" means a DNA fragment comprising a region (transcribed region), which is transcribed into an RNA molecule (e.g. a pre-mRNA or ncRNA) in a cell. The transcribed region can be operably linked to suitable regulatory regions (e.g. a promoter), which form part of the gene as defined herein. A gene can comprise several operably linked fragments, such as a 5' leader sequence, a coding region and a 3' non-translated sequence (3' end) comprising a polyadenylation site.

"Expression of a gene" refers to the process wherein a DNA region which is operably linked to appropriate regulatory regions, particularly a promoter, is transcribed into an RNA, and, in case the RNA encodes for a biologically active protein or peptide, is subsequently translated into a biologically active protein or peptide.

The term "operably linked" refers to a linkage of polynucleotide elements in a functional relationship. A nucleic acid is "operably linked" when it is placed into a functional relationship with another nucleotide sequence. For instance, a promoter, or rather a transcription regulatory sequence, is operably linked to a coding sequence if it affects the transcription of the coding sequence. Operably linked may mean that the DNA sequences being linked are contiguous.

"Promoter" refers to a nucleic acid fragment that functions to control the transcription of one or more nucleic acids. A promoter fragment is located upstream (5') with respect to the direction of transcription of the transcription initiation site of the gene, and is structurally identified by the presence of a binding site for DNA-dependent RNA polymerases, transcription initiation site(s) and can further comprise any other DNA sequences, including, but not limited to transcription factor binding sites, repressor and activator protein binding sites, and any other sequences of nucleotides known to one of skill in the art to act directly or indirectly to regulate the amount of transcription from the promoter.

Optionally the term "promoter" may also include the 5' UTR region (5' Untranslated Region) (e.g. the promoter may herein include one or more parts upstream of the translation initiation codon of transcribed region, as this region may have a role in regulating transcription and/or translation). A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells.

The terms "protein" or "polypeptide" are used interchangeably and refer to molecules consisting of a chain of amino acids, without reference to a specific mode of action, size, 3 dimensional structure or origin. A "fragment" or "portion" of a protein may thus still be referred to as a "protein." A protein as defined herein and as used in any method as defined herein may be an isolated protein. An "isolated protein" is used to refer to a protein which is no longer in its natural environment, for example in vitro or in a recombinant bacterial or plant host cell.

The term "regeneration" is herein defined as the formation of a new tissue and/or a new organ from a single plant cell, a callus, an explant, a tissue or an organ. Preferably, the regeneration is at least one of shoot regeneration, ectopic apical meristem formation, or root regeneration. Regeneration can occur through somatic embryogenesis or organogenesis. The regeneration may further include the formation of a new plant from a single plant cell or from e.g. a callus, an explant, a tissue or an organ. The plant cell for regeneration can be an undifferentiated plant cell. The regeneration process hence can occur directly from parental tissues or indirectly, e.g. via the formation of a callus.

"Conditions that allow for regeneration" is herein understood as an environment wherein a plant cell or a tissue can regenerate. Such conditions include at minimum a suitable temperature, nutrition, day/night rhythm and irrigation.

The term "deaminase" refers to an enzyme that catalyzes a deamination reaction. In some embodiments, the deaminase is a cytosine deaminase, catalyzing the hydrolytic deamination of cytosine to uracil. The deaminase may also be an adenine deaminase, catalyzing the deamination of adenine thereby converting it to inosine.

"Sequence" or "Nucleotide sequence": This refers to the order of nucleotides of, or within a nucleic acid. In other words, any order of nucleotides in a nucleic acid may be referred to as a sequence or nucleotide sequence.

The terms "homology", "sequence identity" and the like are used interchangeably herein. Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleotide sequences, as the case may be, as determined by the match between strings of such sequences. "Similarity" between two amino acid sequences is determined by comparing the amino acid sequence and its conserved amino acid substitutes of one polypeptide to the sequence of a second polypeptide.

The term "complementarity" is herein defined as the sequence identity of a sequence to a fully complementary strand (defined herein below, e.g. the second strand). For example, a sequence that is 100% complementary (or fully complementary) is herein understood as having 100% sequence identity with the complementary strand and e.g. a sequence that is 80% complementary is herein understood as having 80% sequence identity to the (fully) complementary strand.

"Identity" and "similarity" can be readily calculated by known methods. "Sequence identity" and "sequence similarity" can be determined by alignment of two peptide or two nucleotide sequences using global or local alignment algorithms, depending on the length of the two sequences. Sequences of similar lengths are preferably aligned using a global alignment algorithm (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BEST-FIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, *PNAS* 89, 915-919). Sequence alignments and scores for percentage sequence identity may be determined using computer programs, such as the GCG Wisconsin Package, Version 10.3, available from Accelrys Inc., 9685 Scranton Road, San Diego, CA 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blosum62 for proteins and DNAFull for DNA). When sequences have substantially different overall lengths, local alignments, such as those using the Smith Waterman algorithm, are preferred.

Alternatively percentage similarity or identity may be determined by searching against public databases, using algorithms such as FASTA, BLAST, etc. Thus, the nucleic acid and protein sequences of the present invention can further be used as a "query sequence" to perform a search against public databases to, for example, identify other family members or related sequences. Such searches can be performed using the BLASTn and BLASTx programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to nucleic acid molecules of the invention. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25(17): 3389-3402. When utilizing BLAST and Gapped BLAST programs, the default parameters of the respective programs (e.g., BLASTx and BLASTn) can be used. See the homepage of the National Center for Biotechnology Information at ncbi.nlm.nih.gov.

A "homolog" of a gene is a further gene by descent from a common ancestral DNA sequence. The term homolog may apply to the relationship between genes separated by the event of speciation (ortholog) or to the relationship between genes separated by the event of genetic duplication (paralog). An "ortholog" of a gene is a gene in a different species that evolved from a common ancestral gene by speciation, and is understood herein as having retained the same function in the course of evolution.

A "target sequence" is to denote an order of nucleotides within a nucleic acid that is to be targeted, e.g. wherein an alteration is to be introduced or to be detected. For example, the target sequence is an order of nucleotides comprised by a first strand of a DNA duplex.

An "endonuclease" is an enzyme that hydrolyses at least one strand of a duplex DNA upon binding to its recognition site. An endonuclease is to be understood herein as a site-specific endonuclease and the terms "endonuclease" and "nuclease" are used interchangeable herein. A restriction endonuclease is to be understood herein as an endonuclease that hydrolyses both strands of the duplex at the same time to introduce a double strand break in the DNA. A "nicking" endonuclease is an endonuclease that hydrolyses only one strand of the duplex to produce DNA molecules that are "nicked" rather than cleaved.

DETAILED DESCRIPTION OF THE INVENTION

The inventors discovered a novel method for effectively modifying DNA in plant cells in a site-specific way, i.e. by using for the first time in plant cells a new type-V CRISPR/nuclease, known as MAD7 or MAD7-nuclease. Surprisingly, in plant cells, the crRNA-guided MAD7-nuclease appeared more effective as compared to a type-V CRISPR/nuclease counterpart, i.e. *Acidominococcus* sp. Cpf1 (As-Cpf1), at 6 out of 7 independent plant target sites within in total 4 different plant genes, and being equally effective at the remainder target site. Until now, Cpf1 has been considered as one of the most, or even the most, effective CRISPR nuclease in plants. Hence, the inventors discovered a more effective new type-V CRISPR/nuclease for DNA modification in plant cells.

Therefore, provided is a method for targeted modification of DNA in a plant cell, comprising contacting the DNA with a crRNA-guided MAD7-nuclease. The DNA may be any type of DNA, endogenous or exogenous to the cell, for example genomic DNA, chromosomal DNA, artificial chromosomes, plasmid DNA, or episomal DNA. The DNA may be nuclear or organellar DNA. Preferably, the DNA is chromosomal DNA, preferably endogenous to the cell. The method of the invention results in altered DNA at a site of interest, also indicated herein as the target sequence, which is preferably within a gene of interest, preferably within a gene at the plants endogenous chromosomal DNA. In other words, the method of the invention preferably results in a genomic modification, which may refer to an epigenetic modification and/or a genetic modification. The terms "alteration" and "modification" are used interchangeably herein. An epigenetic modification is a heritable modification that changes the gene function or activity, without changing the nucleotide sequence. In an embodiment, the modification is a genetic modification. A genetic modification is understood herein as the alteration of the nucleotide sequence within the DNA, such as a deletion, insertion, substitution or conversion of one or more nucleotides.

Preferably, the method for targeted modification of DNA as detailed herein, wherein the method comprises a step of contacting the DNA with a crRNA-guided MAD7-nuclease, is as least as efficient as compared to an identical or nearly identical method, with the exception that a Cpf1 nuclease is used instead of a crRNA-guided MAD7-nuclease. Preferably the Cpf1 nuclease has an amino acid sequence of SEQ ID NO: 6. Hence preferably, the efficiency to generate one or more INDEL mutations in a plant genome is comparable between MAD7 and Cpf1. MAD7 may be more efficient than Cpf1 in generating INDELs in a plant genome, preferably the MAD7 nuclease is at least 1.2, 1.5, 2, 3, 4, 5, 6, 7, 8, 9, 10, 15 or 20 times more efficient than the Cpf1 nuclease, preferably when MAD7 and Cpf1 target the same sequence in a plant genome.

The efficiency of generating INDEL mutations in a plant genome may be expressed as percentage of the reads showing INDELs at the target region.

The method of the invention may further comprise a step of multiplication and/or genotyping using any conventional method known in the art, in order to screen or test for the nucleotide alteration. The method of the invention therefore comprises such step after contacting the DNA with the crRNA-guided MAD7 nuclease. In a preferred embodiment, the cells, preferably the plant cells, comprising the targeted modification as defined herein, may be genotyped using deep-sequencing technologies, such as Illumina or 454 sequencing. Preferably when using the method of the invention at least 0.5%, 0.8%, 1%, 2%, 3%, 4%, 5%, 6%, 7%, 8%, 9%, 10% or more of the total sequencing reads have an INDEL at the target region.

The targeted DNA modification may be within a coding sequence in the plant genome, thereby resulting in a modified protein, e.g. a protein comprising one or more amino acid alterations or a protein comprising a truncation. The targeted DNA modification may be within a noncoding sequence in the plant genome, such as in an intronic sequence or in a sequence encoding a noncoding (nc)RNA. The targeted modification in a noncoding sequence may result in e.g. a modified splice site or an alteration in the regulatory function of a non-coding RNA. The targeted nucleotide alteration may also be in a regulatory sequence resulting in the down or upregulation of gene expression, optionally in knocking out gene expression. The method of the invention may comprise a step of screening or testing for protein modifications and/or protein expression levels. Such screening or testing may be directly on the protein itself or on altered functionality using any conventional means. In addition or alternatively, the DNA modification may result in a phenotypic alteration of the plant cell or plant. Therefore, the method may comprise a step of screening or testing for a phenotypic alteration or characteristic in the plant cell or plant, preferably a step of screening or tested for a phenotypic characteristic as defined herein.

Preferably, the method of the invention results in a genetic modification of a gene of interest.

Gene of Interest

Preferably, a gene of interest (GOI) is a gene that produces or alters a characteristic, preferably a phenotypic characteristic. A plant GOI thus preferably produces or alters a plant characteristic, preferably a phenotypic plant characteristic. The term "plant characteristic" means any characteristic of a plant, plant cell or plant tissue. Preferably, the plant characteristic is selected from the group consisting of plant development, plant growth, yield, biomass production, plant architecture, plant biochemistry, plant physiology, metabolism, survival capacity and stress tolerance. Alternatively or in addition, the plant characteristic is selected from the group consisting of DNA synthesis, DNA modification, endoreduplication, cell cycle, cell wall biogenesis, transcription regulation, signal transduction, storage lipid mobilization, and photosynthesis.

The term "altering a plant characteristic" as used herein encompasses any change in the plant characteristic such as increase, decrease or change in time or place. It is understood herein that the plant GOI can alter the plant characteristic by introducing, increasing, decreasing, or removing the expression of the GOI and/or by modifying the functionality of the encoded protein such as by altering the coding sequence thereby resulting in expression of a modified encoded protein. Whether the plant characteristic is altered due to an introduced expression of the GOI, increased expression of the GOI, decreased expression of the GOI, removed expression of the GOI and/or modified functionality of the encoded protein, is dependent on the type of GOI and/or the type of plant characteristic.

In an embodiment, the targeted modification is genetic modification that alters a plant characteristic. Such modification may be an early stop. Such modification may also be a single nucleotide modification (SNP) resulting in an amino acid change in the translated protein, which may result in a single amino acid change.

Detailed herein below are, non-limiting, examples of plant characteristics that can be modified by the method of the invention as described herein:

"Growth" refers to the capacity of the plant or of plant parts to expand and increase in biomass. Altered growth refers amongst others to altered growth rate, cycling time, the size, expansion or increase of the plant. Additionally and/or alternatively, growth characteristics may refer to cellular processes comprising, but not limited to, cell cycling (entry, progression, exit), cell division, cell wall biogenesis and/or DNA synthesis, DNA modification and/or endoreduplication.

"Yield" refers to the harvestable part of the plant. "Biomass" refers to any part of the plant. These terms also encompass an increase in seed yield, which includes an increase in the biomass of the seed (seed weight) and/or an increase in the number of (filled) seeds and/or in the size of the seeds and/or an increase in seed volume, each relative to corresponding wildtype plants. An increase in seed size and/or volume may also influence the composition of the seed. An increase in seed yield could be due to an increase in the number and/or size of flowers. An increase in yield may also increase the harvest index, which is expressed as a ratio of the total biomass over the yield of harvestable parts, such as seeds.

"Plant development" means any cellular process of a plant that is involved in determining the developmental fate of a plant cell, in particular the specific tissue or organ type into which a progenitor cell will develop. Typical plant characteristics according to the present invention are therefore characteristics relating to cellular processes relevant to plant development such as for example, morphogenesis, photomorphogenesis, shoot development, root development, vegetative development, reproductive development, stem elongation, flowering, regulatory mechanisms involved in determining cell fate, pattern formation, differentiation, senescence, time of flowering and/or time to flower.

Plant architecture", as used herein refers to the external appearance of a plant, including any one or more structural features or a combination of structural features thereof. Such structural features include the shape, size, number, position, colour, texture, arrangement, and patternation of any cell, tissue or organ or groups of cells, tissues or organs of a plant, including the root, stem, leaf, shoot, petiole, trichome, flower, petal, stigma, style, stamen, pollen, ovule, seed, embryo, endosperm, seed coat, aleurone, fibre, fruit, cambium, wood, heartwood, parenchyma, aerenchyma, sieve element, phloem or vascular tissue, amongst others.

The term "stress tolerance" is understood as the capability of better survival and/or better performance in stress conditions such as environmental stress, which can be biotic or abiotic. Salinity, drought, heat, chilling and freezing are all described as examples of conditions which induce osmotic stress. The term "environmental stress" as used in the present invention refers to any adverse effect on metabolism, growth or viability of the cell, tissue, seed, organ or whole plant which is produced by a non-living or non-biological environmental stressor. More particularly, it can encompass environmental factors such as water stress (flooding, water logging, drought, dehydration), anaerobic stress (low level of oxygen, $CO_2$ etc.), aerobic stress, osmotic stress, salt stress, temperature stress (hot/heat, cold, freezing, frost) or nutrient deprivation, pollutant stress (heavy metals, toxic chemicals), ozone, high light, pathogen (including viruses, bacteria, fungi, insects and nematodes) and combinations of these. Biotic stress is stress as a result of the impact of a living organism on the plant. Examples are stresses caused by pathogens (virus, bacteria, nematodes insects etc.). Another example is stress caused by an organism, which is not necessarily harmful to the plant, such as the stress caused by a symbiont or an epiphyte. Accordingly, particular plant characteristics obtained by modification of the GOI can encompass early vigour, survival rate, and stress tolerance.

Characteristics related to "plant physiology" can encompass characteristics of functional processes of a plant, including developmental processes such as growth, expansion and differentiation, sexual development, sexual reproduction, seed set, seed development, grain filling, asexual reproduction, cell division, dormancy, germination, light adaptation, photosynthesis, leaf expansion, fiber production, secondary growth or wood production, amongst others; responses of a plant to externally-applied factors such as metals, chemicals, hormones, growth factors, environment and environmental stress factors (e.g. anoxia, hypoxia, high temperature, low temperature, dehydration, light, day length, flooding, salt, heavy metals, amongst others), including adaptive responses of plants to said externally-applied factors. Particular plant physiology characteristics which are altered by the GOI identified in the method of the invention can further encompass altered storage lipid mobilization, photosynthesis, transcription regulation and signal transduction.

Plant characteristics related to "plant biochemistry" are to be understood by those skilled in the art to preferably refer to the metabolic characteristics. "Metabolism" can be used interchangeably with biochemistry. Metabolism and/or biochemistry encompass catalytic or assimilation or other metabolic processes of a plant, including primary and secondary metabolism and the products thereof, including any element, small molecules, macromolecules or chemical compounds, such as but not limited to starches, sugars, proteins, peptides, enzymes, hormones, growth factors, nucleic acid molecules, celluloses, hemicelluloses, calloses, lectins, fibres, pigments such as anthocyanins, vitamins, minerals, micronutrients, or macronutrients, that are produced by plants.

The modification of the GOI can be identified by determining the altered plant characteristic, preferably by determining at least one or more altered plant characteristics as defined herein above. In an embodiment, the plant cell having the preferred altered plant characteristic is selected and isolated from plant cells not having the altered plant characteristic. The plant cell can first be generated into a plant prior to selecting the plant having the altered plant characteristic.

The plant cell or plant having an altered plant characteristic can be sequenced to identify and/or further analyse the gene of interest. The skilled person understands that the whole plant genome can be sequenced or a part of the plant genome. In an embodiment, at least the modified sequence is determined.

Preferably, in those cases wherein the modification of the GOI results in an altered plant characteristic, the modification identifies a gene of interest. Therefore the method of the invention can be used in order to screen for gene functionality.

crRNA-quided MAD7-Nuclease

The MAD7-nuclease or the protein of the crRNA-guided MAD7-nuclease complex may be a MAD7-nuclease obtainable from *Eubacterium rectale*, or any homolog or ortholog thereof. Preferably the MAD7-nuclease has an amino acid sequence that has at least about 50%, 60%, 70%, 80%, 85%, 90%, 91%, 92%, 93%, 94%, 95%, 96%, 97%, 98%, 99%, or 100% identity to SEQ ID NO: 1. Preferably, the MAD7-nuclease is a protein that is encoded by a nucleotide sequence having at least about 50%, 60%, 70%, 80%, 85% 90%, 91%, 92%, 93%, 94%, 95%, 96%, 97%, 98%, 99%, or 100% identity to SEQ ID NO: 2. Preferably, the MAD7-nuclease is a protein that is encoded by a nucleotide sequence having at least about 50%, 60%, 70%, 80%, 85% 90%, 91%, 92%, 93%, 94%, 95%, 96%, 97%, 98%, 99%, or 100% identity to SEQ ID NO: 74.

The crRNA is capable of complexing with the MAD7-endonuclease and can hybridize with a target sequence, thereby directing the nuclease to the target sequence. A subject nuclease capable of complexing with a guide nucleic acid can be referred to as a nuclease that is compatible with the guide nucleic acid. Likewise, a guide nucleic acid capable of complexing with a nuclease can be referred to as a guide nucleic acid that is compatible with the nucleases. Preferably the crRNA is RNA but may also comprise DNA. The MAD7-endonuclease thus may form a complex with the crRNA, resulting in a crRNA-guided MAD7-nuclease.

The crRNA can comprise or consist of non-modified or naturally occurring nucleotides. Alternatively, the crRNA can comprise or consist of modified or non-naturally occurring nucleotides, preferably such chemically modified nucleotides are for protecting the crRNA against degradation.

In an embodiment of the invention, the crRNA comprises ribonucleotides and non-ribonucleotides. The crRNA can comprise one or more ribonucleotides and one or more deoxyribonucleotides.

The crRNA may comprise one or more non-naturally occurring nucleotides or nucleotide analogues, such as a nucleotide with phosphorothioate linkage, a locked nucleic acid (LNA) nucleotides comprising a methylene bridge between the 2' and 4' carbons of the ribose ring, bridged nucleic acids (BNA), 2'-O-methyl analogues, 2'-deoxy analogues, 2'-fluoro analogues or combinations thereof. The modified nucleotides may comprise modified bases selected from the group consisting of, but not limited to, 2-aminopurine, 5-bromo-uridine, pseudouridine, inosine, and 7-methylguanosine.

The crRNA may be chemically modified by incorporation of 2'-O-methyl (M), 2'-O-methyl 3'phosphorothioate (MS), 2'-O-methyl 3'thioPACE (phosphonoacetate) (MSP), or a combination thereof, at one or more terminal nucleotides. Such chemically modified crRNAs can comprise increased stability and/or increased activity as compared to unmodified crRNAs. (Hendel et al, 2015, *Nat Biotechnol.* 33(9); 985-989). In certain embodiments, a crRNA comprises ribonucleotides in a region that binds to a target DNA and one or more deoxyribonucleotides and/or nucleotide analogues in a region that binds to the MAD7-nuclease. In an embodiment of the invention, deoxyribonucleotides and/or nucleotide analogues can be incorporated in engineered crRNA structures, such as, without limitation, in the guide sequence, the scaffolding sequence and/or in between the guide and scaffolding sequences. Alternatively or in addition, the chemically modified nucleotides can be located 5' of the scaffolding sequence and/or 3' or the guide sequence.

Preferably, the crRNA for guiding or targeting the MAD7-nuclease to the target sequence in the DNA comprises or consists of a scaffolding and guide sequence, preferably said scaffolding sequence is at, or close to, its 5' end and the guide sequence is at, or close to, its 3' end. Preferably, said scaffolding sequence has a sequence that is at least about 50%, 60%, 70%, 80%, 90%, 95%, 96%, 97%, 98%, 99%, or 100% identical to any one of SEQ ID NO: 21-24, preferably SEQ ID NO: 24. Alternatively, the scaffolding sequence has a sequence that is at least about 50%, 60%, 70%, 80%, 90%, 95%, 96%, 97%, 98%, 99%, or 100% identical to SEQ ID NO:73.

The guide sequence is designed to have sufficient complementarity with the target sequence to hybridize with the target sequence and direct sequence-specific binding of a complexed Mad-7 nuclease to the target sequence. Said target sequence preferably is within a GOI as defined herein. The target sequence is adjacent to a protospacer adjacent motif (PAM) sequence, which preferably is a T-rich motif, preferably TTTN, wherein N can be any one of T, G, A or C. The skilled person is capable of engineering the crRNA to target any desired target sequence, preferably by engineering the guide sequence to be complementary to any desired target sequence, in order to hybridize thereto. Preferably, the complementarity between a guide sequence and its corresponding target sequence, when optimally aligned using a suitable alignment algorithm, is at least about 70%, 80%, 85%, 90%, 91%, 92%, 93%, 94%, 95%, 96%, 97%, 98% or 100%. The guide sequence may be at least about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is about 10-30 nucleotides in length, or about 15-20 nucleotides in length. Preferably the guide sequence is 15, 16, 17, 18, 19, 20, 21, 22, 23, 24 or 25 nucleotides in length, preferably 21 nucleotides.

The MAD7-nuclease may comprise endogenous catalytic activity, thereby being capable of introducing a DSB, or may be engineered to comprise at least one catalytically inactive domain, e.g. one active and one inactive domain. Said MAD7-nuclease may be modified to have an inactive Nuc domain rendering a MAD7-nickase, e.g. an MAD7-R1173A, or an inactive RuvC domain rendering a catalytically inactive MAD7, e.g. MAD7-D1213A, or any homolog or ortholog of MAD7 having a mutation at a similar or equivalent position. Such catalytically inactive MAD7-nuclease may serve to guide a (fused) functional domain as detailed herein below to a specific site in the DNA as determined by the crRNA.

The MAD7-nuclease, or MAD7-nickase or catalytically inactive MAD7-nuclease may be fused to a functional domain. Optionally, such functional domain is for epigenetic modification, for example a histone modification domain. The domains for epigenetic modification can be selected from the group consisting of a methyltransferase, a demethylase, a deacetylase, a methylase, a deacetylase, a deoxygenase, a glycosylase and an acetylase (Cano-Rodriguez et al, *Curr Genet Med Rep* (2016) 4:170-179). The methyltransferase may be selected from the group consisting of G9a, Suv39h1, DNMT3, PRDM9 and Dot1L. The demethylase may be LSD1. The deacetylase may be SIRT6 or SIRT3. The methylase may be at least one of KYP, TgSET8 and NUE. The deacetylase may be selected from the group consisting of HDAC8, RPD3, Sir2a and Sin3a. The deoxygenase may be at least one of TET1, TET2 and TET3, preferably TET1 cd (Gallego-Bartolome J et al, *Proc Natl Acad Sci USA.* (2018); 115(9):E2125-E2134). The glycosylase may be TDG. The acetylase may be p300.

Optionally, the functional domain is a deaminase, or functional fragment thereof, selected from the group consisting of an apolipoprotein B mRNA-editing complex (APOBEC) family deaminase, an activation-induced cytosine deaminase (AID), an ACF1/ASE deaminase, an adenine deaminase, and an ADAT family deaminase. Alternatively or in addition, the deaminase or functional fragment thereof may be ADAR1 or ADAR2, or a variant thereof.

The apolipoprotein B mRNA-editing complex (APOBEC) family of cytosine deaminase enzymes encompasses eleven proteins that serve to initiate mutagenesis in a controlled and beneficial manner. Preferably, the APOBEC deaminase is selected from the group consisting of APOBEC1, APOBEC2, APOBEC3A, APOBEC3B, APOBEC3C, APOBEC3D, APOBEC3F, APOBEC3G, APOBEC3H, APOBEC4 and Activation-induced (cytidine) deaminase. Preferably, the cytosine deaminase of the APOBEC family is activation-induced cytosine (or cytidine) deaminase (AID) or apolipoprotein B editing complex 3 (APOBEC3). These proteins all require a $Zn^{2+}$-coordinating motif (His-X-Glu-X23-26-Pro-Cys-X2_4-Cys) and bound water molecule for catalytic activity. Preferably, in a method of the invention, the deaminase domain of the fused to the MAD7-nuclease is an APOBEC1 family deaminase. Preferably, the deaminase domain is rat deaminase (rAPOBEC1) encoded by a sequence having at least about 80%, 85%, 90%, 95%, 96%, 97%, 98%, 99% or 100% sequence identity with SEQ ID NO: 25 or 37, preferably with SEQ ID NO: 37. In addition or alternatively, the amino acid sequence of the rat deaminase domain has at least about 80%, 85%, 90%, 95%, 96%, 97%, 98%, 99% or 100% sequence identity with SEQ ID NO: 26. Preferably, the deaminase domain has deaminase activity.

Another exemplary suitable type of deaminase domain that may be fused to the MAD7-nuclease is an adenine (or adenosine) deaminase, for example an ADAT family of adenine deaminase. Further, the adenine deaminase may be TadA or a variant thereof, preferably as described in Gaudelli et al., 2017 (Gaudelli et al. 2017 *Nature* 551: 464-471). Preferably, the deaminase domain is TadA encoded by a sequence having at least about 80%, 85%, 90%, 95%, 96%, 97%, 98%, 99% or 100% sequence identity with SEQ ID NO: 27. In addition or alternatively, the amino acid sequence of TadA has at least about 80%, 85%, 90%, 95%, 96%, 97%, 98%, 99% or 100% sequence identity with SEQ ID NO: 28. Preferably, the deaminase domain has deaminase activity. Further, the MAD7-nuclease may be fused to an adenine deaminase domain, e.g. derived from ADAR1 or ADAR2. The deaminase domain of the present invention may comprise or consist of a whole deaminase protein or a fragment thereof which has catalytic activity.

The functional domain, e.g. the deaminase domain, may be fused to the N- or C-terminus of the MAD7-nuclease or catalytically inactive MAD7-nuclease. Preferably, the functional domain is fused to the N-terminus of the MAD7-nuclease. Optionally, the functional domain and the MAD7-nuclease used in the method of the invention are fused directly to each other or via a linker (also denominated herein as a spacer).

The linker may be any suitable linker in the art, e.g., ranging from very flexible linkers of the form (GGGGS)n (SEQ ID NO: 75), (GGS)n (SEQ ID NO: 76), and (G)n (SEQ ID NO: 77) to more rigid linkers of the form (EAAAK)n (SEQ ID NO: 29), (SPKKKRKVEAS)n (SEQ ID NO: 30), or (SGSETPGTSESATPES)n (SEQ ID NO: 31), or (KSGSETPGTSESATPES)n (SEQ ID NO: 32), or any variant thereof, wherein n preferably is between 1 and 7, i.e. 1, 2, 3, 4, 5, 6, or 7.

The linker preferably has a length between 2 and 30 amino acids, or between 3 and 23 amino acids, or between 3 and 18 amino acids.

Optionally, the MAD7-nuclease is further fused to an UDG inhibitor (UGI) domain. The UGI domain may be fused to the N- or C-terminus of the MAD7-nuclease. Preferably, the deaminase domain is fused to the C-terminus of the MAD7-nuclease. The fusion may be direct or via a linker as indicated above. Preferably, the MAD7-nuclease is fused to a deaminase domain at the N-terminus of the MAD7-nuclease, and the MAD7-nuclease is fused to a UGI domain at the C-terminus of the MAD7-nuclease.

Uracil DNA glycosylases (UDGs) recognize uracil, inadvertently present in DNA and initiates the uracil excision repair pathway by cleaving the N-glycosidic bond between the uracil and the deoxyribose sugar, releasing uracil and leaving behind a basic site (AP-site). The AP-site is then processed and restored to a canonical base by the subsequent actions of AP-endonuclease, dRPase, DNA polymerase and DNA ligase enzymes. By fusing a UGI domain to the cytosine deaminase containing MAD7-nuclease fusion protein, the efficiency of base editing increases. Preferably, the UGI domain is or is a variant of UGI from *B. subtilis* bacteriophage PBS1 or PBS2 (UniProtKB—P14739). Preferably, the nucleotide sequence of the UGI domain may have at least about 80%, 85%, 90%, 95%, 96%, 97%, 98%, 99% or 100% sequence identity with SEQ ID NO: 33 or 35, preferably with SEQ ID NO: 35. Preferably, the amino acid sequence of the UGI domain may have at least about 80%, 85%, 90%, 95%, 96%, 97%, 98%, 99% or 100% sequence identity with SEQ ID NO: 34 or 36, preferably with SEQ ID NO: 36. Preferably, the UGI domain inhibits UDG.

In an embodiment, the UDG inhibitor is not fused to the MAD7-nuclease protein as defined herein, but is contacted to the DNA to be edited as a further functional protein, preferably together with the crRNA-guided MAD7-nuclease. In this embodiment, the cell, preferably the plant cell, may be transfected using the UDG inhibitor or a construct encoding the UDG inhibitor. In the latter case, said construct may further comprise a sequence encoding the MAD7-nuclease (fusion) protein as defined herein, or alternatively, the UDG inhibitor and MAD7-nuclease (fusion) protein may be encoded on separate constructs.

The invention also pertains to the use of a MAD7-nuclease or nucleic acid encoding the same, and/or a crRNA for guiding said MAD7-nuclease as defined herein or nucleic acid encoding the same, in a method of the invention, i.e. for use in modifying a plant cell DNA and/or for stably expressing a plant cell.

Oligonucleotide Mediated Targeted Nucleotide
Exchange (ODTNE)

In an embodiment, the crRNA-guided MAD7-nuclease as defined herein is capable of introducing a single-stranded or double stranded break. In this embodiment, the method of the invention may further comprise a step of introducing into the plant cell single-stranded oligonucleotide having a sequence that is at least partly complementary to a target sequence. Such single-stranded oligonucleotide can also be annotated as a template oligonucleotide. Within the context of the current invention "single-stranded" refers to a linear stretch of nucleotides, with a 5'end and a 3'end, without the presence of its fully complementary strand.

Preferably, the single-stranded oligonucleotide comprises the target sequence except for at least one mismatch with respect to the target sequence. In other words, the single-stranded oligonucleotide comprises the information with respect to the alteration that is to be introduced in the target sequence of the DNA to be modified in the method of the invention. In addition to the target sequence with the one or more mismatches, the single-stranded oligonucleotide, may, in certain embodiment also comprise additional stretches of nucleotides adjacent to the target sequence with the one or more mismatches. However, preferably the oligonucleotide substantially consists of the target sequence with the one or more mismatches relative to the target sequence comprised in the first strand of the DNA duplex. Preferably, the single-stranded oligonucleotide comprises at least one mismatch with respect to the PAM sequence preferably present in the target sequence. Preferably, the single-stranded oligonucleotide comprises at least one mismatch with respect to the PAM sequence preferably present in the target sequence, and in addition at least one mismatch outside said PAM sequence. Preferably said at least one mismatch outside said PAM sequence, is a mismatch resulting in a codon alteration, which preferably results in an amino acid change, or early stop, in the encoded protein.

The use of ODTNE and the structure and design of the oligonucleotides that are functional in this technology are well described, inter alia in WO98/54330, WO99/25853, WO01/24615, WO01/25460, WO2007/084294, WO2007/073149, WO2007/073166, WO2007/073170 WO2009/002150, WO2012/074385, WO2012/074386, WO2018/115389 and WO2015/139008. The skilled person thus has a straightforward understanding of how to design the first and second oligonucleotide for use in the current invention.

The mutagenic oligonucleotides used in the present invention preferably have a length that is in line with other mutagenic oligonucleotides used in the art, i.e. typically between 10-60 nucleotides, preferably 20-55 nucleotides, more preferably 25-50 nucleotides. The single-stranded oligonucleotide can comprise a chemical modification, e.g. to make the oligonucleotides at least partly resistant to nucleases.

In an embodiment, the oligonucleotide comprises at least about 18, 20, 22, 24, 26, 28, 30, 32, 34, 36, 38, 40, 42, 44, 46, 48, or at least about 50 contiguous nucleotides that have 100% sequence identity with respectively at least about 18, 20, 22, 24, 26, 28, 30, 32, 34, 36, 38, 40, 42, 44, 46, 48, or at least about 50 contiguous nucleotides of the DNA comprising the target sequence, preferably have 100% sequence identity with respectively at least about 18, 20, 22, 24, 26, 28, 30, 32, 34, 36, 38, 40, 42, 44, 46, 48, or at least about 50 contiguous nucleotides of the DNA comprising the target sequence.

The single-stranded oligonucleotide may comprise both RNA and DNA nucleotides, preferably the single-stranded oligonucleotide does not comprise RNA nucleotides. Preferably, the single-stranded oligonucleotide consists of DNA nucleotides. In some embodiments, as will be detailed herein, one or more of the nucleotides of the single-stranded oligonucleotide comprise chemical modifications. Preferably, the single-stranded oligonucleotide is a chemically protected oligonucleotide, preferably comprising at least one, two, three or four chemically protected nucleotides. Such a chemically protected oligonucleotide may be more resistant to nucleases and may in addition provide for higher binding affinity.

The type of modifications to provide a chemically protected oligonucleotide is not in particular limited. Examples of suitable modifications include the introduction of a reverse base (idC) at the 3' end of the oligonucleotide to create a 3' blocked end on the repair oligonucleotide; introduction of one or more 2'O-methyl nucleotides or bases which increase hybridization energy (see WO2007/073149) at the 5' and/or 3' of the repair oligonucleotide; conjugated (5' or 3') intercalating dyes such as acridine, psoralen, and ethidium bromide; introduction of a 5' terminus cap such as a T/A clamp, a cholesterol moiety, SIMA (HEX), and riboC; backbone modifications such as phosphothioate, methyl phosphonates, MOE (methoxyethyl), di PS and peptide nucleic acid (PNA); or ribose modifications such as 2' 0 methyl and locked nucleic acids (LNA). Preferred chemical modifications are either phosphorothioates (PS) that help to protect the single-stranded oligonucleotide from degradation (PS are normally placed at the ends of the single-stranded oligonucleotide) or locked nucleic acids (LNAs) that give both protection against nucleases and also a higher binding affinity (LNAs can be placed either at the ends of the single-stranded oligonucleotide or internally).

Preferably the at least one mismatch is not a chemically protected nucleotide. According to another preference a chemically protected nucleotide is at least one nucleotide from the at least one mismatch. In other words, preferably a mismatch in the single-stranded oligonucleotide is not a chemically protected nucleotide and the nucleotide adjacent to (either side) the mismatch is also not a chemically protected (or modified) nucleotide.

Homologous Recombination

In an embodiment, the crRNA-guided MAD7-nuclease as defined herein is capable of introducing a single-stranded or double stranded break, e.g. because the nuclease comprises, preferably endogenous, nuclease activity. In this embodiment, the method of the invention may further comprise a step of introducing into the plant cell a double-stranded oligonucleotide, a double stranded DNA, or a double-stranded DNA fragment (donor fragment) having a sequence that is at least partly complementary to a sequence of the DNA to be modified by the method of the invention and comprising the target sequence. Such double-stranded oligonucleotide or DNA is annotated herein as a "donor construct" or a "donor nucleotide", which are used interchangeably herein.

The double-stranded oligonucleotide can be used to modify the sequence of the DNA as defined herein, preferably by means of homologous recombination. Hence, the double-stranded oligonucleotide preferably comprises a sequence at its 3'-end and at its 5'-end that has 100% sequence identity or 100% sequence complementarity with a sequence in the DNA to be modified. Preferably, the sequence in the DNA that is identical to the double-stranded oligonucleotide is located immediately adjacent to the cleavage site generated by the crRNA-guided MAD7-nuclease.

In the presence of the homologous sequence, which can either be the sister chromatid, the donor fragment or the double-stranded oligonucleotide, the DSB can be repaired by homologous recombination (HR). This is the basis for the process of gene targeting whereby, rather than the sister chromatid being used for repair, information is copied from a double-stranded oligonucleotide or donor fragment that is introduced into the cell. The double-stranded oligonucleotide or donor fragment contains alterations or an exogenous sequence compared with the original chromosomal locus, and thus the process of HR incorporates these alterations or exogenous sequence in the genome. Preferably, the exogenous sequence to be introduced by HR is located within the double-stranded oligonucleotide or donor fragment in between the sequences at its 3'-end and at its 5'-end that has 100% sequence identity or 100% sequence complementarity with a sequence in the DNA.

The double-stranded oligonucleotide or double-stranded DNA, or DNA fragment, can be linearized or circular. Preferably, the double-stranded oligonucleotide is a linearized molecule. The first and/or second double-stranded oligonucleotide can comprise a chemical modification, e.g. to make the oligonucleotides at least partly resistant to nucleases. Preferably, the double-stranded oligonucleotide comprises RNA, DNA or is an RNA-DNA hybrid. Preferably, the double-stranded oligonucleotide comprises DNA.

Introducing the crRNA-Quided MAD7-Nuclease

The method of the invention comprises the step of contacting the DNA of the plant cell with crRNA-guided MAD7-nuclease. This may be accomplished by introducing into the plant cell a MAD7-nuclease and crRNA for guiding the MAD7-nuclease to the DNA. The method of the invention may therefore also be defined as a method for targeted modification of DNA in a plant cell, comprising the step of introducing into the plant cell a MAD7-nuclease and crRNA for guiding the MAD7-nuclease to the DNA. The MAD7-nuclease and crRNA may be delivered in the plant cell directly in the form of the MAD7-nuclease protein and/or crRNA (preferably as pre-assembled ribonucleo-protein complexes), as mRNA encoding the MAD7-nuclease and/or crRNA and/or precursor crRNA into a cell, or as one or more nucleic acids encoding the MAD7-nuclease protein and/or crRNA. The latter may be performed by the transfection of one or more vectors comprising a gene encoding the MAD7-nuclease and/or crRNA, wherein the vectors are for the transient expression of said gene and/or crRNA. The introduction in the plant cell or transfection may be performed by any conventional method known in the art. Optionally, sequences encoding MAD7 and/or crRNA(s) are stably introduced in the genome of the plant cell. In case the MAD7-nuclease and crRNA are delivered in the cell as a ribonucleo-protein complex, the method of the invention further comprises the step of forming said complex prior to the step of introducing said complex in the plant cell.

Optionally, the method further comprises a step of introducing a single-stranded oligonucleotide for ODTNE as defined herein or a step of introducing a double-stranded oligonucleotide or donor fragment for HR as defined herein. Optionally, the MAD7-nuclease protein or construct encoding the protein, crRNA or construct encoding the crRNA, and single-stranded oligonucleotide for ODTNE or double-stranded oligonucleotide or donor fragment for HR, are introduced in the plant cell in a single step, i.e. at substantially the same time. In other words, preferably, the MAD7-nuclease protein or construct encoding the protein, crRNA or construct encoding the crRNA, and single-stranded oligonucleotide for ODTNE or double-stranded oligonucleotide or donor fragment for HR are introduced in the plant cell in a single transfection step. Optionally, these components are transfected in two or more transfections steps.

The MAD7-nuclease protein may contain one or more nuclear localization signal sequences (NLS), mutations, deletions, alterations or truncations. Preferably, the NLS-linked MAD7-nuclease protein has an amino acid sequence that has at least about 50%, 60%, 70%, 80%, 85% 90%, 91%, 92%, 93%, 94%, 95%, 96%, 97%, 98%, 99%, or 100% identity to SEQ ID NO: 3. Preferably, the NLS-linked MAD7-nuclease is a protein that is encoded by a nucleotide sequence having at least about 50%, 60%, 70%, 80%, 85% 90%, 91%, 92%, 93%, 94%, 95%, 96%, 97%, 98%, 99%, or 100% identity to SEQ ID NO: 4. In addition, the MAD7-nuclease encoding genes may be codon optimized, e.g. for expression in plants, comprise transcription regulatory sequences and may be driven by either a constitutive, inducible, tissue-specific or species-specific promoter when applicable. Preferably, by a constitutive, inducible, tissue-specific or species-specific promoter that is suitable for expression in plant cells. Preferably, the codon optimized NLS-linked MAD7-nuclease encoding sequence has at least about 50%, 60%, 70%, 80%, 85% 90%, 91%, 92%, 93%, 94%, 95%, 96%, 97%, 98%, 99%, or 100% identity to SEQ ID NO: 4.

Exemplary transcript termination and polyadenylation signals are either NosT, RBCT, HSP18.2T or other gene specific or species-specific terminators. The MAD7-nuclease gene cassettes or mRNA may contain introns, either native or in combination with gene-specific promoters and or synthetic promoters.

In a preferred embodiment, the cell is transformed with at least one MAD7-nuclease, i.e. the MAD7-nuclease protein is delivered directly into the cell. In a further embodiment, the cell is transformed with at least one crRNA. Optionally, the cell is transformed with one MAD7-nuclease and two or more crRNAs, wherein each crRNA comprises a different guide sequence, i.e. targets a different sequence within the plant genome. Preferably, the method of the invention comprises a step of complexing the MAD7-nuclease protein with at least one crRNA before introducing the MAD7-nuclease and crRNA in the cell. In such embodiment, the crRNA-guided MAD7-nuclease is introduced in the plant cell as a complex. Optionally, said introduction step also comprise the introduction of a single-stranded oligonucleotide for ODTNE as defined herein, or a double-stranded oligonucleotide or donor fragment for HR as defined herein.

In another preferred embodiment, the cell is transfected with a nucleic acid construct encoding at least one MAD7-nuclease. The cell may further be transfected with an additional nucleic acid construct encoding at least one crRNA, wherein optionally, said nucleic acid constructs encodes for two or more crRNAs, wherein each crRNA comprises a different guide sequence, i.e. targets a different sequence within the plant genome. Preferably, within this embodiment, the cell is transfected with a single construct encoding at least one MAD7-nuclease and one or more crRNAs as defined herein. Preferably, the nucleotide sequence encoding the MAD7-nuclease protein and the nucleotide sequence encoding the crRNA are under control of different promoters. For example, the MAD7-nuclease protein may, preferably, be under control of a constitutive promoter, preferably suitable for expression in plant, such as the 35 S promoter (e.g. the 35 S promoted from cauliflower mosaic virus (CaMV; Odell et al. *Nature* 313:810-812; 1985). Other suitable constitutive promoters include, but are not limited to, the cassava vein mosaic virus (CsVMV) promoter, and the sugarcane bacilliform badnavirus (ScBV) promoter (see e.g. Samac et al. *Transgenic Res.* 2004 August; 13(4):349-61.) Other constitutive promoters include, for example, the core promoter of the Rsyn7 promoter and other constitutive promoters disclosed in WO 99/43 838 and U.S. Pat. No. 6,072,050; ubiquitin (Christensen et al., *Plant Mol. Biol.* 12:619-632, 1989 and Christensen et al., *Plant Mol. Biol.* 18:675-689, 1992); pEMU (Last et al., *Theor. Appl. Genet.* 81:581-588, 1991); AA6 promoter (WO2007/069894); and the like. The nucleic acid constructs may also include transcription termination regions. Where transcription termination regions are used, any termination region may be used in the preparation of the nucleic acid constructs. In a preferred embodiment, the nucleic acid construct is for transient expression. In other words, the expression in the plant material is temporary as a consequence of the non-permanent presence of the nucleic acid construct. Expression may, for instance, be transient when the construct is not integrated into the host genome. For example, MAD7-nuclease protein and crRNA may be transiently provided to a plant cell, followed by a decline in the amount of either or both of the components. Subsequently, the plant cell, progeny of the plant cell, and plants which comprise the plant cell or have been derived from the plant protoplast wherein the duplex DNA has been altered, comprise a reduced amount of either or both of the components used in the method of the invention, or no longer contain one or more of the components. Preferably, said plant cell, progeny of the plant cell, and plants which comprise the plant cell or have been derived from the plant protoplast wherein the duplex DNA has been altered, still comprise the DNA modification.

The nucleic acid construct encoding the MAD7-nuclease may be optimized for increased expression in the trans-formed plant, i.e. codon-optimized for expression in the plant cell. For instance, the nucleotide sequence encoding the MAD7-nuclease may be codon-optimized for expression in tomato, wherein said tomato preferably is *Solanum lycopersicum*. That is, the nucleic acid construct encoding the MAD7-nuclease protein can be synthesized using plant-preferred codons for improved expression. See, for example, Campbell and Gowri, (*Plant Physiol.* 92: 1-11, 1990) for a discussion of host-preferred codon usage. Methods are available in the art for synthesizing plant-preferred genes (see, for example, Murray et al., *Nucleic Acids Res.* (1989) 17:477-498, or Lanza et al. (2014) *BMC Systems Biology* 8:33-43).

The invention also pertains to nucleic acids and/or constructs encoding MAD7-endonuclease as defined herein, wherein said coding sequence is preferably characterized in that it is codon optimized for expression plant cells, such as but not limited to expression in *Solanum Lycopersicum*. Preferably, the coding sequence has at least about at least

*about* 50%, 60%, 70%, 80%, 85% 90%, 91%, 92%, 93%, 94%, 95%, 96%, 97%, 98%, 99%, or 100% identity to SEQ ID NO: 2 and/or the coding sequence has at least about at least about 50%, 60%, 70%, 80%, 85% 90%, 91%, 92%, 93%, 94%, 95%, 96%, 97%, 98%, 99%, or 100% identity to SEQ ID NO: 74.

The invention also pertains to nucleic acids and/or constructs encoding one or more crRNAs as defined herein, which are characterized in that the guide sequence is for targeting a sequence in the plant genome, preferably a sequence within the GOI as defined herein. The crRNAs may comprise a scaffolding sequence as defined herein.

Such nucleic acids may be single-stranded, double stranded, or partially double-stranded; nucleic acid molecules that comprise one or more free ends, no free ends (e.g., circular); nucleic acid molecules that comprise DNA, RNA, or both; and other varieties of polynucleotides known in the art. Expression vectors according to the invention is suitable for introducing gene expression in a cell, preferably a plant cell. A preferred expression vector is a naked DNA, a DNA complex or a viral vector, wherein the DNA molecule can be a plasmid. A plasmid refers to a circular double stranded DNA loop into which additional DNA segments can be inserted, such as by standard molecular cloning techniques. A DNA complex can be a DNA molecule coupled to any carrier suitable for delivery of the DNA into the cell. A preferred carrier is selected from the group consisting of a lipoplex, a liposome, a polymersome, a polyplex, a dendrimer, an inorganic nanoparticle, a virosome and cell-penetrating peptides. In a preferred embodiment the expression vector is a viral vector, preferably a Tobacco Rattle Virus (TRV), a Bean yellow dwarf virus (BeYDV), a Cabbage leaf curl virus (CaLCuV), a tobravirus and a Wheat dwarf virus (WDV). Preferably, the viral vector is a Tobacco Rattle Virus as defined herein above.

The invention further pertains to a composition comprising one or more, preferably two or more crRNAs as defined herein. Preferably, the crRNA, or crRNAs, is/are characterized in that the guide sequence is for targeting a sequence in the plant genome, preferably a sequence within the GOI as defined herein. The crRNA, or crRNAs, may comprise a scaffolding sequence as defined herein.

There are many suitable approaches known in the art for delivering the nucleic acids (encoding the MAD7-nuclease and/or (encoding) the crRNAs) or the proteins or ribonucleo-protein complexes into the cell. The delivery system may for example constitute a viral-based delivery system or a non-viral delivery system.

Non-limiting examples of non-viral delivery systems include chemical-based transfection (e.g. using calcium phosphate, dendrimers, cyclodextrin, polymers, liposomes, or nanoparticles), non-chemical-based methods (e.g. electroporation, cell squeezing, sonoporation, optical transfection, protoplast fusion, impalefection, heat shock and hydrodynamic delivery), particle-based methods (e.g. a gene gun or magnet-assisted transfection) and bacterial-based delivery systems (e.g. *agrobacterium*-mediated delivery). Non-limiting examples of a viral delivery system includes lentivirus and adenovirus.

In a preferred embodiment, the nucleic acids and/or proteins are introduced into the cell using an aqueous medium, wherein the aqueous medium comprises PEG. Any suitable method can be used, preferably the medium has a pH value of between 5-8, preferably between 6-7.5. Next to the presence in the aqueous medium of the MAD7-nuclease and optionally the crRNA, the medium comprises polyethylene glycol. Polyethylene glycol (PEG) is a polyether compound with many applications from industrial manufacturing to medicine. PEG is also known as polyethylene oxide (PEO) or polyoxyethylene (POE). The structure of PEG is commonly expressed as H—(O—CH2-CH2)n-OH. Preferably, the PEG used is an oligomer and/or polymers, or mixtures thereof with a molecular mass below 20,000 g/mol.

The aqueous medium comprising the population of e.g. plant cells preferably comprises 100-400 mg/ml PEG. So the final concentration of PEG is preferably between 100-400 mg/ml, for example, between 150 and 300 mg/ml, for example between 180 and 250 mg/ml. A preferred PEG is PEG 4000 Sigma-Aldrich no. 81240. (i.e. having an average Mn 4000 (Mn, the number average molecular weight is the total weight of all the polymer molecules in a sample, divided by the total number of polymer molecules in a sample.). Preferably the PEG used as a Mn of about 1000-10 000, for example between 2000-6000).

In a further preferred embodiment, the aqueous medium comprising PEG does not comprise more than about 0.001%, 0.01%, 0.05%, 0.1%, 1%, 2%, 5%, 10% or 20% (v/v) glycerol. Preferably, the medium comprises less than about 0.001%, 0.01%, 0.05%, 0.1%, 1%, 2%, 5%, 10% or 20% (v/v) glycerol. In particular for the introduction of a MAD7-nuclease protein, the aqueous medium comprises less than about 0.1% (for example, less than 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% (v/v) glycerol. Optionally, the aqueous medium comprising the population of plant cells is completely free of glycerol.

Preferably, the cell cycle of e.g. plant cells is synchronized when exposing the duplex DNA to the crRNA-guided MAD7-nuclease. The synchronization preferably takes places when the crRNA-guided MAD7-nuclease or nucleic acid(s) encoding the same is introduced into the cell as detailed herein. Synchronization is preferably performed by contacting the (plant) cell with a synchronizing agent.

Such method of synchronizing the cell cycle of the (plant) cell has been described in detail in European patent EP2516652, incorporated herein by reference. More particular, synchronizing the (plant) cells, for example, the plant protoplasts may be advantageous in certain embodiments of the invention to further enhance efficacy of the introduction of the alteration in the duplex DNA. Thus, in certain embodiments, the method comprises a step of synchronizing the cell cycle of the cell, preferably a plant cell.

The synchronization preferably takes places when the crRNA-guided MAD7-nuclease or nucleic acid(s) encoding the same is introduced into the cell as detailed herein, such that most of the (plant) cells will be in the same phase of the cell cycle when the duplex DNA is exposed to the site-specific nucleases as defined herein. This may be advantageous and increase the rate of introduction of the alteration in the duplex DNA.

Synchronizing the (plant) cell may be accomplished by any suitable means. For example, synchronization of the cell cycle may be achieved by nutrient deprivation such as phosphate starvation, nitrate starvation, ion starvation, serum starvation, sucrose starvation, auxin starvation.

Synchronization can also be achieved by adding a synchronizing agent to the (plant) cell. Preferably, the synchronizing agent is selected from the group consisting of aphidocolin, hydroxyurea, thymidine, colchicine, cobtorin, dinitroaniline, benefin, butralin, dinitramine, ethalfluralin, oryzalin, pendimethalin, trifluralin, amiprophos-methyl, butamiphos dithiopyr, thiazopyr propyzamide, tebutam DCPA (chlorthal-dimethyl), mimosine, anisomycin, alpha amanitin, lovastatin, jasmonic acid, abscisic acid, menadione, cryptogeine, hydrogenperoxide, sodiumpermanganate, indomethacin, epoxomycin, lactacystein, icrf 193, olomoucine, roscovitine, bohemine, staurosporine, K252a, okadaic acid, endothal, caffeine, MG 132, cycline dependent kinases and cycline dependent kinase inhibitors, as well as their target mechanism. The amounts and concentrations and their associated cell cycle phase are described for instance in "Flow Cytometry with plant cells", J. Dolezel c.s. Eds. Wiley-VCH Verlag 2007 pp 327 ff. Preferably, the synchronizing agent is aphidicolin and/or hydroxyurea.

Preferably, in the method of the invention, synchronizing the cell cycle synchronizes the (plant) cell in the S-phase, the M-phase, the G1 and/or G2 phase of the cell cycle.

In a preferred embodiment, the MAD7-nuclease comprises two catalytically active endonuclease domains. Within this embodiment, the crRNA-guided MAD7-nuclease will introduce a double-strand break in the target sequence. Subsequent activation of the repair mechanism results in alteration of the target sequence of the plant genome. The targeted alteration may comprise the insertion, deletion or modification of at least one base pair. For example, the targeted alteration may comprise the deletion of at least one base pair and the insertion of at least one base pair. For example, 1, 2, 3, 4, 5, 6, 7, 8, 9, 10 or more base pairs may be altered with the method of the invention. More than one modification may be introduced in a single experiment, and/or the experiment may be repeated to introduce subsequent alterations in the genome of the plant cell, optionally at other or at the same gene as targeted in the first event.

The invention further pertains to a method for targeted alteration of a coding sequence (CDS) in duplex DNA, preferably as described in PCT/EP2018/074150 which is incorporated herein by reference, wherein the method comprises a step of exposing the duplex DNA to at least two crRNA-guided MAD7 nucleases, wherein a first site-specific nuclease cleaves the DNA generating a first indel at a first location within the ORF and wherein a second site-specific nuclease cleaves the DNA generating a second indel at a second location within the same CDS, wherein the CDS before the first indel and after the second indel remain in the same reading frame, and wherein the altered CDS does not comprise a stop codon.

Plant Cell

The method of the invention may further comprise the step of providing a plant cell, preceding the step of introducing into said plant cell a MAD7-nuclease and crRNA for guiding the MAD7-nuclease as defined herein. The skilled person understands that the method of the invention is not limited to a certain plant cell type. In particular, the method of the invention as disclosed herein can be applied to dividing as well as non-dividing cells. The cell may be transgenic or non-transgenic. The plant cell can for example be obtainable from plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, grains and the like.

In a preferred embodiment, the plant cell is a plant protoplast. The skilled person is aware of methods and protocols for preparing and propagating plant protoplasts, see for example Plant Tissue Culture (ISBN: 978-0-12-415920-4, Roberta H. Smith). The plant protoplasts for use in the method of the current invention can be provided using common procedures used for the generation of plant cell protoplasts (e.g. the cell wall may be degraded using cellulose, pectinase and/or xylanase).

Plant cell protoplasts systems have for example been described for tomato, tobacco and many more (*Brassica napus, Daucus carota, Lactucca sativa, Zea mays, Nicotiana benthamiana, Petunia hybrida, Solanum tuberosum, Oryza sativa*). The present invention is generally applicable to any protoplast system, including those, but not limited to, the systems described in any one of the following references: Barsby et al. 1986, *Plant Cell Reports* 5(2): 101-103; Fischer et al. 1992, *Plant Cell Rep.* 11(12): 632-636; Hu et al. 1999, *Plant Cell, Tissue and Organ Culture* 59: 189-196; Niedz et al. 1985, *Plant Science* 39: 199-204; Prioli and Sondahl, 1989, *Nature Biotechnology* 7: 589-594; S. Roest and Gilissen 1989, *Acta Bot. Neerl.* 38(1): 1-23; Shepard and Totten, 1975, *Plant Physiol.*55: 689-694; Shepard and Totten, 1977, *Plant Physiol.* 60: 313-316, which are incorporated herein by reference.

The plant cell is preferably obtainable from a crop plant such as a monocot or dicot or of a crop or grain plant such as cassava, corn, sorghum, soybean, wheat, oat or rice. A crop plant is plant species which is cultivated and bred by humans. A crop plant may be cultivated for food purposes (e.g. field crops), or for ornamental purposes (e.g. production of flowers for cutting, grasses for lawns, etc.). A crop plant as defined herein also includes plants from which non-food products are harvested, such as oil for fuel, plastic polymers, pharmaceutical products, cork and the like.

The plant cell may also be of an alga, tree or production plant, fruit or vegetable (e.g., trees such as citrus trees, e.g., orange, grapefruit or lemon trees; peach or nectarine trees; apple or pear trees; nut trees such as almond or walnut or pistachio trees; nightshade plants; plants of the genus *Brassica*; plants of the genus *Lactuca*; plants of the genus *Spinacia*; plants of the genus *Capsicum*; plants of the genus *Solanum*, preferably *Solanum lycopersicum*).

In another preferred embodiment, the cell is obtainable from a plant selected from the group consisting of asparagus, barley, blackberry, blueberry, broccoli, cabbage, canola, carrot, cassava, cauliflower, chicory, cocoa, coffee, cotton, cucumber, eggplant, grape, hot pepper, lettuce, maize, melon, oilseed rape, pepper, potato, pumpkin, raspberry, rice, rye, sorghum, spinach, squash, strawberry, sugar cane, sugar beet, sunflower, sweet pepper, tobacco, tomato, water melon, wheat, and zucchini.

Preferably, the obtained plant cell comprising the targeted alteration is regenerated into a plant or descendent therefore. Therefore in a preferred embodiment of the invention, the method further comprises a step of regenerating a plant or descendent thereof comprising the targeted alteration.

Plant Cell and Plant or Plant Products

The method may further comprise the step of regenerating a plant or descendent thereof comprising the targeted modification. Preferably, such regeneration is performed using conditions suitable for regeneration. The skilled person is well aware of methods and protocols of regenerating a plant from a plant protoplast. Progeny, descendant's, variants, and mutants of the regenerated plants are also included within the scope of the invention, provided that these parts comprise the targeted alteration introduced with the method taught herein.

In addition to the plant cell or plant comprising the targeted modification, the invention also pertains to a plant cell transiently or stably expressing MAD7-endonuclease. Preferably, the plant cell is a transgenic plant modified to comprise a sequence encoding MAD7-endonuclease in its genome as defined herein. Included within the scope of the invention is such transgenic plant cell and plant regenerated thereof, any progeny, descendant's, variants, and mutants comprising the sequence encoding MAD7-endonuclease, preferably under the control of an inducible promoter and/or a meristem promoter which may be constitutive active meristem promoter. The invention therefore also pertains to a method for producing such transgenic plant cell and/or plant derived therefrom comprising the step of integrating into its genome the MAD7-endonuclease encoding sequence as defined herein.

The cell or organism obtainable by a method of the invention may subsequently be propagated to e.g. obtain a culture of cells, (part of) an organism or any descendants thereof.

Preferably, the cell is a plant cell obtainable from a crop plant such as a monocot or dicot or of a crop or grain plant such as cassava, corn, sorghum, soybean, wheat, oat or rice. The plant cell may also be of an alga, tree or production plant, fruit or vegetable (e.g., trees such as citrus trees, e.g., orange, grapefruit or lemon trees; peach or nectarine trees; apple or pear trees; nut trees such as almond or walnut or pistachio trees; nightshade plants; plants of the genus *Brassica*; plants of the genus *Lactuca*; plants of the genus *Spinacia*; plants of the genus *Capsicum*; plants of the genus *Solanum*, preferably *Solanum lycopersicum*).

In another preferred embodiment, the cell is obtainable from a plant selected from the group consisting of *Arabidopsis*, asparagus, barley, blackberry, blueberry, broccoli, cabbage, canola, carrot, cassava, cauliflower, chicory, cocoa, coffee, cotton, cucumber, eggplant, grape, hot pepper, lettuce, maize, melon, oilseed rape, pepper, potato, pumpkin, raspberry, rice, rye, sorghum, spinach, squash, strawberry, sugar cane, sugar beet, sunflower, sweet pepper, tobacco, tomato, water melon, wheat, and zucchini.

The invention also pertains to the progeny of a plant cell or plant obtainable by a method of the invention. Further, the invention pertains to a plant product obtainable from the plant cell or plant as defined herein, e.g. fruits, leaves, plant organs, plant fats, plant oils, plant starch, and plant protein fractions, either crushed, milled or still intact, mixed with other materials, dried, frozen, and so on. These products may be non-propagating. Preferably, said plant product comprises at least or at least part of one of:

i) the modified DNA, preferably the modified GOI as defined herein, or encoded products thereof, ii) the MAD7-nuclease as define herein, and iii) the MAD7-nuclease encoding sequence.

Preferably, these products comprise at least fractions of modified DNA the MAD7-nuclease or encoding sequence, which allows to assess that the plant product is derived from a plant obtained by a method as defined herein.

Kit of Parts

The invention also concerns a kit of parts, preferably a kit of parts for use in the method as described herein. Preferably, the kit of parts comprises at least one of:

A container comprising a MAD7-nuclease as defined herein;

A container comprising a crRNA for guiding the MAD7-nuclease as defined herein, a single-stranded oligonucleotide for ODTNE as defined herein, a double-stranded oligonucleotide for HR as defined herein, or any combination thereof. Preferably, the container comprises two or more crRNAs each comprising different guide sequences for targeting different target sequences;

A container comprising one or more nucleic acid constructs or vectors encoding a MAD7-nuclease as defined herein. Optionally, said construct or vector further encodes one or more crRNAs for guiding said MAD7-nuclease as defined herein; and A container comprising one or more nucleic acid constructs or vectors encoding one or more crRNAs for guiding said MAD7-nuclease as defined herein.

The kit of parts may further comprise a container comprising one or more substances for transfection as defined herein. Also included within the kit may be a manual for performing the method of the invention of modifying a DNA within the plant cell as specified herein.

The reagents may be present in lyophilized form, or in an appropriate buffer. The kit may also contain any other component necessary for carrying out the present invention, such as buffers, pipettes, microtiter plates and written instructions. Such other components for the kits of the invention are known to the skilled person.

Having now generally described the invention, the same will be more readily understood through reference to the following example which is provided by way of illustration and is not intended to be limiting of the present invention.

Example 1

Use of MAD7 to Generate Targeted Mutations in Tomato

Constructs

The sequences of the type-V CRISPR nucleases MAD7 and AsCpf1, which have been optimized for translation in tomato, are presented by SEQ ID NO: 3 and SEQ ID NO: 5 for the protein sequence of MAD7 and AsCpf1, respectively, and by SEQ ID NO: 4 and SEQ ID NO: 6 for the nucleotide sequence encoding the Mad7 and AsCpf1 protein, respectively. These ORFs were synthesized and then cloned in a vector behind the constitutive 35S promoter for expression in plant cells. The sequences of the crRNA cassettes used (U6 promoter crRNA) are shown in table 1. These were also synthesized and cloned into a vector. All of the plasmid constructs were introduced into *E. coli* and then transformed colonies were used to inoculate 50 ml cultures. After overnight growth plasmid DNA was isolated from these cultures using standard methods.

TABLE 1

Sequences of the crRNA cassettes.
Sequences of the crRNA cassettes are represented herein by SEQ ID NO: 7-20.
The Arabidopsis U6 promoter sequence is underlined, the non-variant
crRNA sequence is shown in bold and the targeting sequence is shown in italics.
Each crRNA is followed by seven thymine bases that act as a polIII terminator.
Target site 1 and 2 are in PDS1, target site 3 and 4 are in LIN5, target
site 5 and 6 are in eIF4e and target site 7 is in ETR1.

| SEQ ID NO: | Description | Sequence |
|---|---|---|
| SEQ ID NO: 7 | KG10731 (crRNA 1 for guiding MAD7 to target site 1) | GGAGTGATCAAAAGTCCCACATCGATCAGGTGATATAT AGCAGCTTAGTTTATATAATGATAGAGTCGACATAGCGA TTGTCAAAAGACCTTTTTAATTTCTACTCTTGTAGATAC TTCTGAGGTTTGTGGATCT TTTTTTT |
| SEQ ID NO: 8 | KG10732 (crRNA 2 for guiding MAD7 to target site 2) | GGAGTGATCAAAAGTCCCACATCGATCAGGTGATATAT AGCAGCTTAGTTTATATAATGATAGAGTCGACATAGCGA TTGTCAAAAGACCTTTTTAATTTCTACTCTTGTAGATAG TTCCCAAAGAAGACGACCT TTTTTTT |
| SEQ ID NO: 9 | KG10733 (crRNA 3 for guiding MAD7 to target site 3) | GGAGTGATCAAAAGTCCCACATCGATCAGGTGATATAT AGCAGCTTAGTTTATATAATGATAGAGTCGACATAGCGA TTGTCAAAAGACCTTTTTAATTTCTACTCTTGTAGATAT CGTCAGGTAATACATCGGA TTTTTTT |
| SEQ ID NO: 10 | KG10734 (crRNA 4 for guiding MAD7 to target site 4) | GGAGTGATCAAAAGTCCCACATCGATCAGGTGATATAT AGCAGCTTAGTTTATATAATGATAGAGTCGACATAGCGA TTGTCAAAAGACCTTTTTAATTTCTACTCTTGTAGATGC CATACTTGTCGCGGAATAC TTTTTTT |
| SEQ ID NO: 11 | KG10735 (crRNA 5 for guiding MAD7 to target site 5) | GGAGTGATCAAAAGTCCCACATCGATCAGGTGATATAT AGCAGCTTAGTTTATATAATGATAGAGTCGACATAGCGA TTGTCAAAAGACCTTTTTAATTTCTACTCTTGTAGATTG GACCAAGAATGCTGCAAAT TTTTTTT |
| SEQ ID NO: 12 | KG10736 (crRNA 6 for guiding MAD7 to target site 6) | GGAGTGATCAAAAGTCCCACATCGATCAGGTGATATAT AGCAGCTTAGTTTATATAATGATAGAGTCGACATAGCGA TTGTCAAAAGACCTTTTTAATTTCTACTCTTGTAGATAT TTGCAGCATTCTTGGTCCA TTTTTTT |
| SEQ ID NO: 13 | KG10737 (crRNA 7 for guiding MAD7 to target site 7) | GGAGTGATCAAAAGTCCCACATCGATCAGGTGATATAT AGCAGCTTAGTTTATATAATGATAGAGTCGACATAGCGA TTGTCAAAAGACCTTTTTAATTTCTACTCTTGTAGATTC CATTCCAGTGGAGTTGATA TTTTTTT |
| SEQ ID NO: 14 | KG9943 (crRNA 1.1 for guiding AsCpf1 to target site 1) | GGAGTGATCAAAAGTCCCACATCGATCAGGTGATATAT AGCAGCTTAGTTTATATAATGATAGAGTCGACATAGCGA TTTAATTTCTACTCTTGTAGATACTTCTGAGGTTTGTGG ATCTTTTTTTT |
| SEQ ID NO: 15 | KG9942 (crRNA 2.1 for guiding AsCpf1 to target site 2) | GGAGTGATCAAAAGTCCCACATCGATCAGGTGATATAT AGCAGCTTAGTTTATATAATGATAGAGTCGACATAGCGA TTTAATTTCTACTCTTGTAGATAGTTCCCAAAGAAGACG ACCTTTTTTTT |
| SEQ ID NO: 16 | KG10533 (crRNA 3.1 for guiding AsCpf1 to target site 3) | GGAGTGATCAAAAGTCCCACATCGATCAGGTGATATAT AGCAGCTTAGTTTATATAATGATAGAGTCGACATAGCGA TTTAATTTCTACTCTTGTAGATATCGTCAGGTAATACAT CGGATTTTTTT |
| SEQ ID NO: 17 | KG10106 (crRNA 4.1 for guiding AsCpf1 to target site 4) | GGAGTGATCAAAAGTCCCACATCGATCAGGTGATATAT AGCAGCTTAGTTTATATAATGATAGAGTCGACATAGCGA TTTAATTTCTACTCTTGTAGATGCCATACTTGTCGCGGA ATACTTTTTTT |
| SEQ ID NO: 18 | KG10101 (crRNA 5.1 for guiding AsCpf1 to target site 5) | GGAGTGATCAAAAGTCCCACATCGATCAGGTGATATAT AGCAGCTTAGTTTATATAATGATAGAGTCGACATAGCGA TTTAATTTCTACTCTTGTAGATTGGACCAAGAATGCTGC AAATTTTTTTT |
| SEQ ID NO: 19 | KG10102 (crRNA 6.1 for guiding AsCpf1 to target site 6) | GGAGTGATCAAAAGTCCCACATCGATCAGGTGATATAT AGCAGCTTAGTTTATATAATGATAGAGTCGACATAGCGA TTTAATTTCTACTCTTGTAGATATTTGCAGCATTCTTGG TCCATTTTTTT |

TABLE 1-continued

Sequences of the crRNA cassettes.
Sequences of the crRNA cassettes are represented herein by SEQ ID NO: 7-20.
The Arabidopsis U6 promoter sequence is underlined, the non-variant
crRNA sequence is shown in bold and the targeting sequence is shown in italics.
Each crRNA is followed by seven thymine bases that act as a polIII terminator.
Target site 1 and 2 are in PDS1, target site 3 and 4 are in LIN5, target
site 5 and 6 are in elF4e and target site 7 is in ETR1.

| SEQ ID NO: | Description | Sequence |
|---|---|---|
| SEQ ID NO: 20 | KG10104 (crRNA 7.1 for guiding AsCpf1 to target site 7) | GGAGTGATCAAAAGTCCCACATCGATCAGGTGATATAT AGCAGCTTAGTTTATATAATGATAGAGTCGACATAGCGA TTTAATTTCTACTCTTGTAGAT*TCCATTCCAGTGGAGTT* *GATATTTTTTT* |

Tomato Protoplast Isolation and Transfection

In vitro shoot cultures of *Solanum lycopersicon* var Moneyberg were maintained on MS20 medium with 0.8% agar in high plastic jars at 16/8 h photoperiod of 2000 lux at 25° C. and 60-70% RH. Young leaves (1 g) were gently sliced perpendicularly to the mid nerve to ease the penetration of the enzyme mixture. Sliced leaves were transferred to the enzyme mixture (2% Cellulase Onozuka RS, 0.4% Macerozyme Onozuka R10 in CPW9M) and cell wall digestion was allowed to proceed overnight in the dark at 25° C. The protoplasts were filtered through a 50 μm nylon sieve and were harvested by centrifugation for 5 minutes at 800 rpm. Protoplasts were resuspended in CPW9M (Frearson, 1973) medium and 3 mL CPW18S (Frearson et al. 1973. *Developmental Biology*, 33:130-137) was added at the bottom of each tube using a long-neck glass Pasteur pipette. Live protoplasts were harvested by centrifugation for 10 minutes at 800 rpm as the cell fraction at the interface between the sucrose and CPW9M medium. Protoplasts were counted and resuspended in MaMg (Negrutiu et al. 1987. *Plant Molecular Biology*, 8: 363-373) medium at a final density of $10^6$ per mL.

For the protoplast transfections 10 μg of a MAD7 or AsCpf1 expression plasmid and 20 μg of one of the sgRNA expressing plasmids were mixed with 500 μL (500000 protoplasts) of the protoplast suspension and 500 μL of PEG solution (400 g/l poly(ethylene glycol) 4000, Sigma-Aldrich #81240; 0.1 M Ca(NO$_3$)$_2$) was then added and the transfection was allowed to take place for 20 minutes at room temperature. Control samples were also produced by omitting one or both of the plasmids from the transfection. Then, 10 mL of 0.275 M Ca(NO$_3$)$_2$ solution was added and thoroughly, but gently mixed in. The protoplasts were harvested by centrifugation for 5 minutes at 800 rpm and resuspended in 9M culture medium at a density of $0.5×10^6$ per ml and transferred to a 4 cm diameter petri dish and an equal volume of 2% alginate solution (20 g/l Alginate-Na (Sigma-Aldrich #A0682), 0.14 g/l CaCl$_2$·2H$_2$O, 90 g/l mannitol) was added. Then 1 ml aliquots (125000 transfected protoplasts) were spread over Ca-Agar plates (72.5 g/l mannitol, 7.35 g/l CaCl$_2$·2H$_2$O, 8 g/l agar, pH5.8) and allowed to polymerize for 1 hour. The alginate disc containing the embedded protoplasts was then transferred to a 4 cm tissue culture dish containing 4 ml of K8p (Kao et al. 1975. *Planta*, 126: 105-110) culture medium. To determine the frequency of indel formation at the target sequences the disc of transfected protoplasts was removed from the dish after 48 hours, the alginate was dissolved, and the protoplasts were isolated by centrifugation. For the regeneration of calli, the protoplasts are incubated in the K8p medium for 21 days at 28° C. in the dark. After this period the discs of transfected protoplasts are transferred to solid GM medium (Tan et al. 1987. *Plant Cell Reports*, 6: 172-175) supplemented with 1 mg·l$^{-1}$ zeatin, 0.2 mg·l$^{-1}$ GA3 and 20 nM chlorsulfuron. The discs are then transferred to fresh plates of the same GM medium every 3 weeks until the surviving calli are large enough to be picked with tweezers and are subsequently grown for genotyping on GM medium. Once calli containing mutations at the target site are identified then they are regenerated into fertile plants. Calli are maintained on GM medium without the herbicide until the first shoots develop. The shooting calli are then placed on MS medium supplemented with 2 mg·l$^{-1}$ zeatin and 0.1 mg·l$^{-1}$ IAA media. After some time the regenerated tomato plantlets can be excised and rooted on MS medium supplemented with 0.5 mg·l$^{-1}$ IBA before transfer to the greenhouse.

Genotyping Protoplasts and Calli

Total genomic DNA was isolated from tomato protoplasts (48 hrs post transfection) using the DNeasy Plant Mini Kit (Qiagen). This gDNA was then used in a PCR reaction to amplify either the target regions. The PCR products were then used as templates to generate a library from each sample which were then pooled and sequenced using a 126 nt paired run on the MiSeq platform (Illumina). Each sample was identified using a unique 5 bp tag. After sequencing the reads derived from each sample were processed to identify the number and types of sequence changes present at the target site. To identify calli with mutations at the target site the transfected protoplasts are regenerated to calli approximately 3 mm in diameter. A direct PCR kit (Phire Plant Direct PCR kit, Thermo Scientific) is then used together with gene specific primers to amplify the target sequence from each callus. The resulting PCR products are then sequenced or genotyped in a different way identify the calli that have mutations at the target site. These calli are then selected for regeneration.

Results

We tested the ability of the class V-CRISPR nuclease MAD7 to generate INDEL mutations in the genome plant cells by expressing the MAD7 protein and crRNAs targeting seven different sequences ectopically in tomato protoplasts. First a MAD7 ORF optimized for codon usage in tomato was constructed together with a nuclear localization signal (NLS) fused at the C terminus. This was then cloned behind the constitutive CaMV 35S promoter for expression in plant cells. The MAD7 protein requires the presence of a PAM sequence adjacent to the targeted sequence, in this case TTTN, which is identical to the PAM of another class V-CRISPR nuclease AsCpf1 that has been reported to be effective in plant cells as well as other eukaryotic cell types. This common PAM sequence allows the design of crRNAs for both MAD7 and AsCpf1 containing exactly the same target sequence so that a direct comparison of the mutagenesis efficiencies produced by each nuclease can be performed. Vectors for the expression of either MAD7 or AsCpf1 were introduced into tomato mesophyll protoplasts together with a second vector expressing a crRNA driven by the *Arabidopsis thaliana* U6 promoter. In such a system the MAD7 or AsCpf1 mRNA and the crRNA will be expressed at high levels for a short period, 24-48 hours, at which point the introduced plasmids will become degraded by cellular nucleases and CRISPR reagents will disappear from the cell. While they are present they are able to find the specific target site in the genome and create INDEL mutations. The introduced plasmids rarely integrate into the genome and so this approach does not result in transgenic lines. The protoplasts were then cultured for 48 hours and then analyzed by sequencing for the presence of an INDEL at the target site.

In total, seven different target sites were investigated, located in the exons of 4 different genes in the tomato genome (PDS, LIN5, eIF4e and ETR1). As shown in FIG. 1, the MAD7 class V-CRISPR nuclease was able to introduce INDEL mutations at all seven of the target sites at varying efficiencies. Surprisingly, the efficiency of INDEL formation when using MAD7 was in nearly all cases higher than when the same sequence was targeted using the AsCpf1 class V-CRISPR nuclease. Several publications have reported the use of AsCpf1 in plants and other eukaryotic cell types, but our data shows that MAD7 is unexpectedly superior and is therefore more suitable for mutagenesis experiments in plants. Table 2 summarizes the types of INDEL mutations that are introduced at the target sites by both MAD7 and AsCpf1. The size and position of the INDELs created by either nuclease are similar and in most cases would lead to the elimination of gene activity (null allele) due to the introduction of a frameshift in the coding sequence. In order to generate plants carrying MAD7 INDEL mutations, tomato mesophyll protoplasts are transfected with the MAD7 expression vector and a crRNA expressing vector for the appropriate target site and then grown to calli. These calli are then genotyped and the ones containing an INDEL mutation regenerated into intact plants.

TABLE 2

INDEL mutations introduced at the target sites by both MAD7 and AsCpf1.
For each sample the enzyme used (MAD7 or AsCpf1) and the crRNA is indicated together with the percentage of total reads that contain an indel. The upper sequence in each sample shows the unmodified target (underlined) with the PAM sequence is shown in bold. The top two most common indels produced in each sample are shown along with the percentage of reads in which they occur.

MAD7 + KG10731 (crRNA 1), 2.85% indels

```
SEQ ID NO: 38    CGTTTAACTTCTGAGGTTTGTGGATCTTTTA
SEQ ID NO: 45    CGTTTAACTTCTGAGGTTT----------TA      0.24%
SEQ ID NO: 46    CGTTTAACTTCTGAGGTTTGT---------A      0.11%
```

AsCpf1 + KG9943 (crRNA 1.1), 2.7% indels

```
SEQ ID NO: 38    CGTTTAACTTCTGAGGTTTGTGGATCTTTTA
SEQ ID NO: 47    CGTTTAACTTCTGAGGTTT----------TA      0.42%
SEQ ID NO: 48    CGTTTAACTTCTGAGGTTT---------TTA      0.28%
```

MAD7 + KG10732 (crRNA 2), 1.07% indels

```
SEQ ID NO: 39    ACTTTCAGTTCCCAAAGAAGACGACCTCGAGCTCC
SEQ ID NO: 49    ACTTTCAGTTCCCAAAGAAGACGA------GCTCC  0.34%
SEQ ID NO: 50    ACTTTCAGTTCCCAAAGAAGAC---CTCGAGCTCC  0.14%
```

AsCpf1 + KG9942 (crRNA 2.2), 0.32% indels

```
SEQ ID NO: 39    ACTTTCAGTTCCCAAAGAAGACGACCTCGAGCTCC
SEQ ID NO: 51    ACTTTCAGTTCCCAAAGAAGACGA------GCTCC  0.06%
SEQ ID NO: 52    ACTTTCAGTTCCCAAAGAAGA---------GCTCC  0.03%
```

MAD7 + KG10733 (crRNA 3), 1.9% indels

```
SEQ ID NO: 40    AATTTCATCGTCAGGTAATACATCGGATTCA
SEQ ID NO: 53    AATTTCATCGTCAGGTAATA--------TCA      0.18%
SEQ ID NO: 54    AATTTCATCGTCAGGTAATAC-----ATTCA      0.16%
```

AsCpf1 + KG10533 (crRNA 3.1), 0.73% indels

```
SEQ ID NO: 40    AATTTCATCGTCAGGTAATACATCGGATTCA
SEQ ID NO: 55    AATTTCATCGTCAGGTAATAC--------CA      0.09%
SEQ ID NO: 56    AATTTCATCGTCAGGTAATA-----GATTCA      0.15%
```

TABLE 2-continued

INDEL mutations introduced at the target sites by
both MAD7 and AsCpf1.
For each sample the enzyme used (MAD7 or AsCpf1) and
the crRNA is indicated together with the percentage
of total reads that contain an indel. The upper
sequence in each sample shows the unmodified target
(underlined) with the PAM sequence is shown in bold.
The top two most common indels produced in each
sample are shown along with the percentage of
reads in which they occur.

MAD7 + KG10734 (crRNA 4), 6.07% indels

| | | |
|---|---|---|
| SEQ ID NO: 41 | GGTTTAGCCATACTTGTCGCGGAATACCTTG | |
| SEQ ID NO: 57 | GGTTTAGCCATACTTGTCG--------CTTG | 0.97% |
| SEQ ID NO: 58 | GGTTTAGCCATACTTGTCGC---------TG | 0.51% |

AsCpf1 + KG10106 (crRNA 4.1), 0.94% indels

| | | |
|---|---|---|
| SEQ ID NO: 41 | GGTTTAGCCATACTTGTCGCGGAATACCTTG | |
| SEQ ID NO: 59 | GGTTTAGCCATACTTGTCGC---------TG | 0.18% |
| SEQ ID NO: 60 | GGTTTAGCCATACTTGTCGC----------G | 0.09% |

MAD7 + KG10735 (crRNA 5), 0.93% indels

| | | |
|---|---|---|
| SEQ ID NO: 42 | GCTTTGTGGACCAAGAATGCTGCAAATGAA | |
| SEQ ID NO: 61 | GCTTTGTGGACCAAGAATG---------AA | 0.24% |
| SEQ ID NO: 62 | GCTTTGTGGACCAAGAATGCTG------AA | 0.16% |

AsCpf1 + KG10101 (crRNA 5.1), 0.05% indels

| | | |
|---|---|---|
| SEQ ID NO: 42 | GCTTTGTGGACCAAGAATGCTGCAAATGAA | |
| SEQ ID NO: 63 | GCTTTGTGGACCAAGA------------AA | 0.01% |
| SEQ ID NO: 64 | GCTTTGTGGACCAAGAATGCTG------AA | 0.03% |

MAD7 + KG10736 (crRNA 6), 0.88% indels

| | | |
|---|---|---|
| SEQ ID NO: 43 | TGTTTCATTTGCAGCATTCTTGGTCCACA | |
| SEQ ID NO: 65 | TGTTTCATTTGCAGCATT---------CA | 0.15% |
| SEQ ID NO: 66 | TGTTTCATTTGCAGCATTC---------- | 0.07% |

AsCpf1 + KG10102 (crRNA 6.1), 0.08% indels

| | | |
|---|---|---|
| SEQ ID NO: 43 | TGTTTCATTTGCAGCATTCTTGGTCCACA | |
| SEQ ID NO: 67 | TGTTTCATTTGCAGCATTCTT-------A | 0.04% |
| SEQ ID NO: 68 | TGTTTCATTTGCAGCATTCT--------- | 0.02% |

MAD7 + KG10737 (crRNA 7), 0.4% indels

| | | |
|---|---|---|
| SEQ ID NO: 44 | TATTTCTCCATTCCAGTGGAGTTGATATACT | |
| SEQ ID NO: 69 | TATTTCTCCATTCCAGTGGAGTT-----ACT | 0.03% |
| SEQ ID NO: 70 | TATTTCTCCATTCCAGTGGA-------TACT | 0.03% |

AsCpf1 + KG10104 (crRNA 7.1), 0.07% indels

| | | |
|---|---|---|
| SEQ ID NO: 44 | TATTTCTCCATTCCAGTGGAGTTGATATACT | |
| SEQ ID NO: 71 | TATTTCTCCATTCCAGTGGA-------TACT | 0.02% |
| SEQ ID NO: 72 | TATTTCTCCATTCCAGTGGA---------CT | 0.02% |

---

The invention claimed is:

1. A method for generating insertion and/or deletion (INDEL) mutations in DNA in a *Solanum lycopersicum* plant cell, comprising the step of:

transiently introducing into the *Solanum lycopersicum* plant cell, a nucleic acid construct encoding a crRNA-guided MAD7-endonuclease, wherein said plant cells are protoplasts of *Solanum lycopersicum*, wherein the nucleic acid construct is introduced into the plant cell using polyethylene glycol (PEG) mediated transfection, and wherein efficiency of MAD7-endonuclease in generating INDEL mutations in the *Solanum lycopersicum* plant cell is at least 1.2 times greater than efficiency of an AsCpf1 nuclease in generating INDEL mutations in a *Solanum lycopersicum* plant cell.

2. The method according to claim 1, wherein the MAD7-endonuclease comprises two catalytically active endonuclease domains.

3. The method according to claim 1, wherein the MAD7-endonuclease comprises at least one catalytically inactive endonuclease domain.

4. The method according to claim 1, wherein the crRNA is introduced in the cell by transfecting the cell with a nucleic acid construct encoding said crRNA.

5. The method according to claim 1, wherein a crRNA is introduced in the cell by transfecting the cell with the crRNA.

6. The method according to claim 1, wherein the cell is further transfected with a template oligonucleotide.

7. The method according to claim 1, wherein the cell is further transfected with a donor construct.

8. The method according to claim 1, wherein the MAD7-endonuclease, crRNA and/or optionally the template oligo-nucleotide or donor construct, are introduced into the plant cell using an aqueous medium comprising PEG.

9. The method according to claim 1, wherein the method further comprises the step of regenerating a *Solanum lycopersicum* plant or descendent thereof comprising the INDEL mutations.

10. The method according to claim 5, wherein the crRNA is chemically modified.

11. The method according to claim 6, wherein the template oligonucleotide is chemically modified.

12. The method according to claim 7, wherein the donor construct is chemically modified.

13. A method for generating insertion and/or deletion (INDEL) mutations in a genome of a *Solanum lycopersicum* plant cell, comprising the steps of:

transiently introducing into a population of plant cells a nucleic acid construct encoding a crRNA-guided MAD7-endonuclease; wherein said plant cells are protoplasts of *Solanum lycopersicum* and culturing the population of plant cells for at least 48 hours to obtain a population of plant cells wherein at least 0.5% of the population comprises the targeted modification INDEL mutations, wherein the nucleic acid construct is introduced into the population of plant cells using polyethylene glycol (PEG) mediated transfection, and wherein efficiency of MAD7-endonuclease in generating INDEL mutations in the *Solanum lycopersicum* plant cell is at least 1.2 times greater than efficiency of an AsCpf1 nuclease in generating INDEL mutations in a *Solanum lycopersicum* plant cell.

* * * * *

SEQUENCE LISTING

<160> NUMBER OF SEQ ID NOS: 77

<210> SEQ ID NO 1
<211> LENGTH: 1263
<212> TYPE: PRT
<213> ORGANISM: Eubacterium rectale

<400> SEQUENCE: 1

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln

-continued

```
                20                    25                    30
Gln Phe Ile Val Lys Asn Gly Ile Ile Lys Glu Asp Glu Leu Arg Gly
            35                    40                    45

Glu Asn Arg Gln Ile Leu Lys Asp Ile Met Asp Asp Tyr Tyr Arg Gly
        50                    55                    60

Phe Ile Ser Glu Thr Leu Ser Ser Ile Asp Asp Ile Asp Trp Thr Ser
65                    70                    75                    80

Leu Phe Glu Lys Met Glu Ile Gln Leu Lys Asn Gly Asp Asn Lys Asp
                    85                    90                    95

Thr Leu Ile Lys Glu Gln Thr Glu Tyr Arg Lys Ala Ile His Lys Lys
                100                   105                   110

Phe Ala Asn Asp Asp Arg Phe Lys Asn Met Phe Ser Ala Lys Leu Ile
            115                   120                   125

Ser Asp Ile Leu Pro Glu Phe Val Ile His Asn Asn Asn Tyr Ser Ala
        130                   135                   140

Ser Glu Lys Glu Glu Lys Thr Gln Val Ile Lys Leu Phe Ser Arg Phe
145                   150                   155                   160

Ala Thr Ser Phe Lys Asp Tyr Phe Lys Asn Arg Ala Asn Cys Phe Ser
                165                   170                   175

Ala Asp Asp Ile Ser Ser Ser Ser Cys His Arg Ile Val Asn Asp Asn
                180                   185                   190

Ala Glu Ile Phe Phe Ser Asn Ala Leu Val Tyr Arg Arg Ile Val Lys
                195                   200                   205

Ser Leu Ser Asn Asp Asp Ile Asn Lys Ile Ser Gly Asp Met Lys Asp
        210                   215                   220

Ser Leu Lys Glu Met Ser Leu Glu Glu Ile Tyr Ser Tyr Glu Lys Tyr
225                   230                   235                   240

Gly Glu Phe Ile Thr Gln Glu Gly Ile Ser Phe Tyr Asn Asp Ile Cys
                245                   250                   255

Gly Lys Val Asn Ser Phe Met Asn Leu Tyr Cys Gln Lys Asn Lys Glu
                260                   265                   270

Asn Lys Asn Leu Tyr Lys Leu Gln Lys Leu His Lys Gln Ile Leu Cys
        275                   280                   285

Ile Ala Asp Thr Ser Tyr Glu Val Pro Tyr Lys Phe Glu Ser Asp Glu
    290                   295                   300

Glu Val Tyr Gln Ser Val Asn Gly Phe Leu Asp Asn Ile Ser Ser Lys
305                   310                   315                   320

His Ile Val Glu Arg Leu Arg Lys Ile Gly Asp Asn Tyr Asn Gly Tyr
                325                   330                   335

Asn Leu Asp Lys Ile Tyr Ile Val Ser Lys Phe Tyr Glu Ser Val Ser
                340                   345                   350

Gln Lys Thr Tyr Arg Asp Trp Glu Thr Ile Asn Thr Ala Leu Glu Ile
            355                   360                   365

His Tyr Asn Asn Ile Leu Pro Gly Asn Gly Lys Ser Lys Ala Asp Lys
        370                   375                   380

Val Lys Lys Ala Val Lys Asn Asp Leu Gln Lys Ser Ile Thr Glu Ile
385                   390                   395                   400

Asn Glu Leu Val Ser Asn Tyr Lys Leu Cys Ser Asp Asp Asn Ile Lys
                405                   410                   415

Ala Glu Thr Tyr Ile His Glu Ile Ser His Ile Leu Asn Asn Phe Glu
                420                   425                   430

Ala Gln Glu Leu Lys Tyr Asn Pro Glu Ile His Leu Val Glu Ser Glu
            435                   440                   445
```

-continued

```
Leu Lys Ala Ser Glu Leu Lys Asn Val Leu Asp Val Ile Met Asn Ala
    450             455             460

Phe His Trp Cys Ser Val Phe Met Thr Glu Glu Leu Val Asp Lys Asp
465             470             475             480

Asn Asn Phe Tyr Ala Glu Leu Glu Glu Ile Tyr Asp Glu Ile Tyr Pro
            485             490             495

Val Ile Ser Leu Tyr Asn Leu Val Arg Asn Tyr Val Thr Gln Lys Pro
            500             505             510

Tyr Ser Thr Lys Lys Ile Lys Leu Asn Phe Gly Ile Pro Thr Leu Ala
        515             520             525

Asp Gly Trp Ser Lys Ser Lys Glu Tyr Ser Asn Asn Ala Ile Ile Leu
    530             535             540

Met Arg Asp Asn Leu Tyr Tyr Leu Gly Ile Phe Asn Ala Lys Asn Lys
545             550             555             560

Pro Asp Lys Lys Ile Ile Glu Gly Asn Thr Ser Glu Asn Lys Gly Asp
            565             570             575

Tyr Lys Lys Met Ile Tyr Asn Leu Leu Pro Gly Pro Asn Lys Met Ile
        580             585             590

Pro Lys Val Phe Leu Ser Ser Lys Thr Gly Val Glu Thr Tyr Lys Pro
        595             600             605

Ser Ala Tyr Ile Leu Glu Gly Tyr Lys Gln Asn Lys His Ile Lys Ser
    610             615             620

Ser Lys Asp Phe Asp Ile Thr Phe Cys His Asp Leu Ile Asp Tyr Phe
625             630             635             640

Lys Asn Cys Ile Ala Ile His Pro Glu Trp Lys Asn Phe Gly Phe Asp
            645             650             655

Phe Ser Asp Thr Ser Thr Tyr Glu Asp Ile Ser Gly Phe Tyr Arg Glu
            660             665             670

Val Glu Leu Gln Gly Tyr Lys Ile Asp Trp Thr Tyr Ile Ser Glu Lys
        675             680             685

Asp Ile Asp Leu Leu Gln Glu Lys Gly Gln Leu Tyr Leu Phe Gln Ile
    690             695             700

Tyr Asn Lys Asp Phe Ser Lys Lys Ser Thr Gly Asn Asp Asn Leu His
705             710             715             720

Thr Met Tyr Leu Lys Asn Leu Phe Ser Glu Glu Asn Leu Lys Asp Ile
            725             730             735

Val Leu Lys Leu Asn Gly Glu Ala Glu Ile Phe Phe Arg Lys Ser Ser
        740             745             750

Ile Lys Asn Pro Ile Ile His Lys Lys Gly Ser Ile Leu Val Asn Arg
        755             760             765

Thr Tyr Glu Ala Glu Glu Lys Asp Gln Phe Gly Asn Ile Gln Ile Val
    770             775             780

Arg Lys Asn Ile Pro Glu Asn Ile Tyr Gln Glu Leu Tyr Lys Tyr Phe
785             790             795             800

Asn Asp Lys Ser Asp Lys Glu Leu Ser Asp Glu Ala Ala Lys Leu Lys
            805             810             815

Asn Val Val Gly His His Glu Ala Ala Thr Asn Ile Val Lys Asp Tyr
            820             825             830

Arg Tyr Thr Tyr Asp Lys Tyr Phe Leu His Met Pro Ile Thr Ile Asn
        835             840             845

Phe Lys Ala Asn Lys Thr Gly Phe Ile Asn Asp Arg Ile Leu Gln Tyr
    850             855             860
```

-continued

```
Ile Ala Lys Glu Lys Asp Leu His Val Ile Gly Ile Asp Arg Gly Glu
865             870             875             880

Arg Asn Leu Ile Tyr Val Ser Val Ile Asp Thr Cys Gly Asn Ile Val
            885             890             895

Glu Gln Lys Ser Phe Asn Ile Val Asn Gly Tyr Asp Tyr Gln Ile Lys
        900             905             910

Leu Lys Gln Gln Glu Gly Ala Arg Gln Ile Ala Arg Lys Glu Trp Lys
    915             920             925

Glu Ile Gly Lys Ile Lys Glu Ile Lys Glu Gly Tyr Leu Ser Leu Val
    930             935             940

Ile His Glu Ile Ser Lys Met Val Ile Lys Tyr Asn Ala Ile Ile Ala
945             950             955             960

Met Glu Asp Leu Ser Tyr Gly Phe Lys Lys Gly Arg Phe Lys Val Glu
            965             970             975

Arg Gln Val Tyr Gln Lys Phe Glu Thr Met Leu Ile Asn Lys Leu Asn
            980             985             990

Tyr Leu Val Phe Lys Asp Ile Ser Ile Thr Glu Asn Gly Gly Leu Leu
        995             1000            1005

Lys Gly Tyr Gln Leu Thr Tyr Ile Pro Asp Lys Leu Lys Asn Val
    1010            1015            1020

Gly His Gln Cys Gly Cys Ile Phe Tyr Val Pro Ala Ala Tyr Thr
    1025            1030            1035

Ser Lys Ile Asp Pro Thr Thr Gly Phe Val Asn Ile Phe Lys Phe
    1040            1045            1050

Lys Asp Leu Thr Val Asp Ala Lys Arg Glu Phe Ile Lys Lys Phe
    1055            1060            1065

Asp Ser Ile Arg Tyr Asp Ser Glu Lys Asn Leu Phe Cys Phe Thr
    1070            1075            1080

Phe Asp Tyr Asn Asn Phe Ile Thr Gln Asn Thr Val Met Ser Lys
    1085            1090            1095

Ser Ser Trp Ser Val Tyr Thr Tyr Gly Val Arg Ile Lys Arg Arg
    1100            1105            1110

Phe Val Asn Gly Arg Phe Ser Asn Glu Ser Asp Thr Ile Asp Ile
    1115            1120            1125

Thr Lys Asp Met Glu Lys Thr Leu Glu Met Thr Asp Ile Asn Trp
    1130            1135            1140

Arg Asp Gly His Asp Leu Arg Gln Asp Ile Ile Asp Tyr Glu Ile
    1145            1150            1155

Val Gln His Ile Phe Glu Ile Phe Arg Leu Thr Val Gln Met Arg
    1160            1165            1170

Asn Ser Leu Ser Glu Leu Glu Asp Arg Asp Tyr Asp Arg Leu Ile
    1175            1180            1185

Ser Pro Val Leu Asn Glu Asn Asn Ile Phe Tyr Asp Ser Ala Lys
    1190            1195            1200

Ala Gly Asp Ala Leu Pro Lys Asp Ala Asp Ala Asn Gly Ala Tyr
    1205            1210            1215

Cys Ile Ala Leu Lys Gly Leu Tyr Glu Ile Lys Gln Ile Thr Glu
    1220            1225            1230

Asn Trp Lys Glu Asp Gly Lys Phe Ser Arg Asp Lys Leu Lys Ile
    1235            1240            1245

Ser Asn Lys Asp Trp Phe Asp Phe Ile Gln Asn Lys Arg Tyr Leu
    1250            1255            1260
```

```
<210> SEQ ID NO 2
<211> LENGTH: 3789
<212> TYPE: DNA
<213> ORGANISM: Artificial Sequence
<220> FEATURE:
<223> OTHER INFORMATION: MAD7 coding sequence codon optimized for S.
      lycopersicum

<400> SEQUENCE: 2
atgaacaacg ggaccaacaa cttccagaac ttcatcggga tcagctccct ccaaaagacc        60
cttaggaacg ctcttatccc aaccgagact acccagcagt tcatcgtgaa gaacgggatc       120
atcaaagagg acgagcttag gggagagaac aggcagatcc tcaaggatat catggacgac       180
tactacaggg gcttcatctc cgagactctg tcctccatcg atgatatcga ctggacctcc       240
ttgttcgaga gatggaaat ccagctcaag aacggggaca acaaggacac ccttatcaaa       300
gagcagaccg agtaccgtaa ggccatccac aaaaagttcg ctaacgacga caggttcaag       360
aatatgttct ccgccaagct catcagcgac atccttccag agttcgtgat ccacaacaac       420
aactactccg cctccgagaa agaggaaaag acccaggtca tcaagctgtt ctccaggttc       480
gctacctcct tcaaggacta cttcaagaac agggccaact gcttctccgc cgacgatatc       540
tcttcatctt cttgccacag gatcgtgaac gacaacgccg agatcttctt ctccaacgct       600
cttgtgtaca ggcgtatcgt gaagtccctc tccaacgatg acatcaacaa gatctccggg       660
gacatgaagg acagcctcaa agagatgtcc ctcgaagaga tctactccta cgagaagtac       720
ggggagttca tcacccaaga gggcatcagc ttctacaacg acatctgcgg aaaggtgaac       780
tccttcatga acctctactg ccagaagaac aaagagaaca gaacctgta caagctccag       840 aagctccaca gcagatcct gtgcattgct gacactagct acgaggtgcc atacaagttc       900
gagtccgatg aagaggtgta ccagtccgtg aatggcttcc tcgacaacat ctcctctaag       960
cacatcgtcg agaggcttag gaagatcggc gataactaca cgggtacaa cctggacaag      1020 atctacatcg tgtccaagtt ctacgagtcc gtgagccaga aaacctaccg tgattgggag      1080
actatcaaca ccgctctcga gattcactac aacaacattc tccccggcaa cgggaaatcc      1140
aaggctgata aggttaagaa ggccgtcaag aacgacctcc agaagtctat cactgagatc      1200
aacgagctgg tgtccaacta caagctctgc tccgatgaca acatcaaggc cgagacttac      1260
atccacgaga tctcccacat cctgaacaac ttcgaggccc aagagctgaa gtacaaccca      1320
gagattcacc tcgtcgagtc tgagcttaag gcctccgagc ttaagaacgt gctcgacgtt      1380
atcatgaacg ccttccattg gtgctccgtg ttcatgactg aagagttggt ggacaaggat      1440
aacaacttct acgccgagct ggaagaaatc tacgacgaga tctaccccgt gatctccctc      1500
tacaacctcg tgaggaatta cgtgacccag aagccatact ccaccaagaa gatcaagctc      1560
aacttcggga tcccaacctt ggctgatgga tggtccaagt ccaaagagta ctccaacaac      1620
gccatcatcc tgatgaggga caacctgtac tacctcggga tcttcaacgc caagaacaag      1680
cccgacaaga agattatcga ggggaacacc tctgagaaca agggcgacta caaaaagatg      1740
atctacaact gctcccaggg cctaacaag atgatcccca aggtgttcct cagctccaag      1800
actggtgttg agacatacaa gccctccgcc tacattctcg aggatacaa gcaaacaag      1860 cacatcaagt cctccaagga cttcgatatc accttctgcc acgacctcat cgattatttc      1920
aagaactgca ttgccattca tccagagtgg aagaacttcg gttcgactt ctccgatacc      1980 tccacctacg aggatatctc cggattctac cgtgaggtta gcttcagggg gtacaagatc      2040
gattggacct acatcagcga gaaggacatc gacctgttgc aagagaaggg gcagctttac      2100
```

```
ctcttccaaa tctacaacaa agacttctcc aaaaagtcca ccggcaacga caacctccac   2160
accatgtacc tcaagaacct cttcagcgaa gagaacctca aggacattgt gctcaagctg   2220
aatggcgagg ctgagatttt ctttaggaag tcctctatca agaaccccat catccacaag   2280
aagggctcca tcctcgttaa caggacttac gaggctgaag agaaggacca gttcgggaac   2340
attcagatcg tgcgtaagaa catccccgag aacatctacc aagagcttta caagtacttc   2400
aacgacaagt ccgacaaaga gctgtctgac gaggctgcca agttgaagaa tgtggtggga   2460
catcatgagg ccgctaccaa cattgtgaag gactacaggt acacttacga caagtatttc   2520
ttgcacatgc ccatcaccat caacttcaag gccaacaaga ccggcttcat caacgacagg   2580
atcctccagt acattgccaa agaaaaggac ctccacgtga tcgggattga taggggtgag   2640
cgaaacctca tctacgtgtc agtgatcgat acctgcggga catcgttga gcagaagtcc   2700 ttcaacatcg ttaacgggta cgactaccag attaagctca gcagcaaga gggtgctaga   2760 cagatcgcta ggaaagagtg gaaagagatc gggaaaatca agagatcaa agaaggctac   2820 ctctccttgg tgattcacga gatcagcaag atggtgatca gtacaacgc tattatcgcc   2880 atggaagatc tcagctacgg cttcaagaag gggcgtttta aggttgagag gcaggtctac   2940
caaaagttcg agactatgct gatcaacaag ctgaactacc tggtgtttaa ggacatctcc   3000
attaccgaga acggcgggct tcttaaggga taccagctca cttacattcc cgacaaactg   3060
aagaacgtgg gtcaccaatg cggctgcatt ttctatgttc cagctgccta cacctccaag   3120
atcgacccaa ctactggatt cgtgaacatc ttcaagttca aggacctcac cgtggacgct   3180
aagagggaat tcatcaagaa gttcgactcc atcaggtacg actccgagaa gaaccttttc   3240
tgcttcacct tcgattacaa caactttatc acccagaaca ccgtgatgtc caagagcagc   3300
tggtcagtgt acacatacgg tgtgaggatc aagcgacgtt tcgtgaacgg aaggttcagc   3360
aacgagagcg atacaatcga catcactaag gacatggaaa agactcttga gatgaccgac   3420
atcaactggc gtgatggtca tgatctcagg caggacatta tcgactacga gatcgtgcag   3480
cacatcttcg aaatcttcag gctcactgtg cagatgagga actcccttag tgagcttgag   3540 gataggggact acgacaggct tatctcccca gtgcttaacg agaacaacat cttctacgac   3600
agcgctaagg ctggggatgc tttgccaaaa gatgctgatg ctaacggggc ttactgtatc   3660
gctttgaagg ggctgtacga gattaagcag atcaccgaga ctggaaagaa ggatggcaag   3720
ttctcccgtg acaagctcaa gatctctaac aaggactggt cgatttcat tcagaacaag   3780 cgttacctc                                                           3789
```

<210> SEQ ID NO 3
<211> LENGTH: 1274
<212> TYPE: PRT
<213> ORGANISM: Artificial Sequence
<220> FEATURE:
<223> OTHER INFORMATION: MAD7-NLS

<400> SEQUENCE: 3

```
Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Asp Tyr Tyr Arg Gly
```

```
                50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
                100                 105                 110

Phe Ala Asn Asp Asp Arg Phe Lys Asn Met Phe Ser Ala Lys Leu Ile
                115                 120                 125

Ser Asp Ile Leu Pro Glu Phe Val Ile His Asn Asn Asn Tyr Ser Ala
                130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Ser Cys His Arg Ile Val Asn Asp Asn
                180                 185                 190

Ala Glu Ile Phe Phe Ser Asn Ala Leu Val Tyr Arg Arg Ile Val Lys
                195                 200                 205

Ser Leu Ser Asn Asp Asp Ile Asn Lys Ile Ser Gly Asp Met Lys Asp
                210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
                260                 265                 270

Asn Lys Asn Leu Tyr Lys Leu Gln Lys Leu His Lys Gln Ile Leu Cys
                275                 280                 285

Ile Ala Asp Thr Ser Tyr Glu Val Pro Tyr Lys Phe Glu Ser Asp Glu
                290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
                340                 345                 350

Gln Lys Thr Tyr Arg Asp Trp Glu Thr Ile Asn Thr Ala Leu Glu Ile
                355                 360                 365

His Tyr Asn Asn Ile Leu Pro Gly Asn Gly Lys Ser Lys Ala Asp Lys
                370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
                420                 425                 430

Ala Gln Glu Leu Lys Tyr Asn Pro Glu Ile His Leu Val Glu Ser Glu
                435                 440                 445

Leu Lys Ala Ser Glu Leu Lys Asn Val Leu Asp Val Ile Met Asn Ala
                450                 455                 460

Phe His Trp Cys Ser Val Phe Met Thr Glu Glu Leu Val Asp Lys Asp
465                 470                 475                 480
```

-continued

```
Asn Asn Phe Tyr Ala Glu Leu Glu Glu Ile Tyr Asp Glu Ile Tyr Pro
                485             490             495

Val Ile Ser Leu Tyr Asn Leu Val Arg Asn Tyr Val Thr Gln Lys Pro
            500             505             510

Tyr Ser Thr Lys Lys Ile Lys Leu Asn Phe Gly Ile Pro Thr Leu Ala
            515             520             525

Asp Gly Trp Ser Lys Ser Lys Glu Tyr Ser Asn Asn Ala Ile Ile Leu
        530             535             540

Met Arg Asp Asn Leu Tyr Tyr Leu Gly Ile Phe Asn Ala Lys Asn Lys
545             550             555             560

Pro Asp Lys Lys Ile Ile Glu Gly Asn Thr Ser Glu Asn Lys Gly Asp
            565             570             575

Tyr Lys Lys Met Ile Tyr Asn Leu Leu Pro Gly Pro Asn Lys Met Ile
            580             585             590

Pro Lys Val Phe Leu Ser Ser Lys Thr Gly Val Glu Thr Tyr Lys Pro
            595             600             605

Ser Ala Tyr Ile Leu Glu Gly Tyr Lys Gln Asn Lys His Ile Lys Ser
        610             615             620

Ser Lys Asp Phe Asp Ile Thr Phe Cys His Asp Leu Ile Asp Tyr Phe
625             630             635             640

Lys Asn Cys Ile Ala Ile His Pro Glu Trp Lys Asn Phe Gly Phe Asp
            645             650             655

Phe Ser Asp Thr Ser Thr Tyr Glu Asp Ile Ser Gly Phe Tyr Arg Glu
            660             665             670

Val Glu Leu Gln Gly Tyr Lys Ile Asp Trp Thr Tyr Ile Ser Glu Lys
            675             680             685

Asp Ile Asp Leu Leu Gln Glu Lys Gly Gln Leu Tyr Leu Phe Gln Ile
        690             695             700

Tyr Asn Lys Asp Phe Ser Lys Lys Ser Thr Gly Asn Asp Asn Leu His
705             710             715             720

Thr Met Tyr Leu Lys Asn Leu Phe Ser Glu Glu Asn Leu Lys Asp Ile
            725             730             735

Val Leu Lys Leu Asn Gly Glu Ala Glu Ile Phe Phe Arg Lys Ser Ser
            740             745             750

Ile Lys Asn Pro Ile Ile His Lys Lys Gly Ser Ile Leu Val Asn Arg
            755             760             765

Thr Tyr Glu Ala Glu Glu Lys Asp Gln Phe Gly Asn Ile Gln Ile Val
    770             775             780

Arg Lys Asn Ile Pro Glu Asn Ile Tyr Gln Glu Leu Tyr Lys Tyr Phe
785             790             795             800

Asn Asp Lys Ser Asp Lys Glu Leu Ser Asp Glu Ala Ala Lys Leu Lys
            805             810             815

Asn Val Val Gly His His Glu Ala Ala Thr Asn Ile Val Lys Asp Tyr
            820             825             830

Arg Tyr Thr Tyr Asp Lys Tyr Phe Leu His Met Pro Ile Thr Ile Asn
            835             840             845

Phe Lys Ala Asn Lys Thr Gly Phe Ile Asn Asp Arg Ile Leu Gln Tyr
        850             855             860

Ile Ala Lys Glu Lys Asp Leu His Val Ile Gly Ile Asp Arg Gly Glu
865             870             875             880

Arg Asn Leu Ile Tyr Val Ser Val Ile Asp Thr Cys Gly Asn Ile Val
            885             890             895
```

-continued

```
Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
        915                 920                 925

Glu Ile Gly Lys Ile Lys Glu Ile Lys Glu Gly Tyr Leu Ser Leu Val
    930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser  Ile Thr Glu Asn Gly  Gly Leu Leu
        995                 1000                1005

Lys Gly  Tyr Gln Leu Thr Tyr  Ile Pro Asp Lys Leu  Lys Asn Val
    1010                1015                1020

Gly His  Gln Cys Gly Cys Ile  Phe Tyr Val Pro Ala  Ala Tyr Thr
    1025                1030                1035

Ser Lys  Ile Asp Pro Thr Thr  Gly Phe Val Asn Ile  Phe Lys Phe
    1040                1045                1050

Lys Asp  Leu Thr Val Asp Ala  Lys Arg Glu Phe Ile  Lys Lys Phe
    1055                1060                1065

Asp Ser  Ile Arg Tyr Asp Ser  Glu Lys Asn Leu Phe  Cys Phe Thr
    1070                1075                1080

Phe Asp  Tyr Asn Asn Phe Ile  Thr Gln Asn Thr Val  Met Ser Lys
    1085                1090                1095

Ser Ser  Trp Ser Val Tyr Thr  Tyr Gly Val Arg Ile  Lys Arg Arg
    1100                1105                1110

Phe Val  Asn Gly Arg Phe Ser  Asn Glu Ser Asp Thr  Ile Asp Ile
    1115                1120                1125

Thr Lys  Asp Met Glu Lys Thr  Leu Glu Met Thr Asp  Ile Asn Trp
    1130                1135                1140

Arg Asp  Gly His Asp Leu Arg  Gln Asp Ile Ile Asp  Tyr Glu Ile
    1145                1150                1155

Val Gln  His Ile Phe Glu Ile  Phe Arg Leu Thr Val  Gln Met Arg
    1160                1165                1170

Asn Ser  Leu Ser Glu Leu Glu  Asp Arg Asp Tyr Asp  Arg Leu Ile
    1175                1180                1185

Ser Pro  Val Leu Asn Glu Asn  Asn Ile Phe Tyr Asp  Ser Ala Lys
    1190                1195                1200

Ala Gly  Asp Ala Leu Pro Lys  Asp Ala Asp Ala Asn  Gly Ala Tyr
    1205                1210                1215

Cys Ile  Ala Leu Lys Gly Leu  Tyr Glu Ile Lys Gln  Ile Thr Glu
    1220                1225                1230

Asn Trp  Lys Glu Asp Gly Lys  Phe Ser Arg Asp Lys  Leu Lys Ile
    1235                1240                1245

Ser Asn  Lys Asp Trp Phe Asp  Phe Ile Gln Asn Lys  Arg Tyr Leu
    1250                1255                1260

Ser Gly  Gly Ser Pro Lys Lys  Lys Arg Lys Val
    1265                1270
```

<210> SEQ ID NO 4
<211> LENGTH: 3825
<212> TYPE: DNA

-continued

```
<213> ORGANISM: Artificial Sequence
<220> FEATURE:
<223> OTHER INFORMATION: MAD7-NLS coding sequence codon optimized for S.
      lycopersicum

<400> SEQUENCE: 4
atgaacaacg ggaccaacaa cttccagaac ttcatcggga tcagctccct ccaaaagacc      60
cttaggaacg ctcttatccc aaccgagact acccagcagt tcatcgtgaa gaacgggatc     120
atcaaagagg acgagcttag gggagagaac aggcagatcc tcaaggatat catggacgac     180
tactacaggg gcttcatctc cgagactctg tcctccatcg atgatatcga ctggacctcc     240
ttgttcgaga gagatggaaat ccagctcaag aacggggaca acaaggacac ccttatcaaa     300
gagcagaccg agtaccgtaa ggccatccac aaaaagttcg ctaacgacga caggttcaag     360
aatatgttct ccgccaagct catcagcgac atccttccag agttcgtgat ccacaacaac     420
aactactccg cctccgagaa agaggaaaag acccaggtca tcaagctgtt ctccaggttc     480
gctacctcct tcaaggacta cttcaagaac agggccaact gcttctccgc cgacgatatc     540
tcttcatctt cttgccacag gatcgtgaac gacaacgccg agatcttctt ctccaacgct     600
cttgtgtaca ggcgtatcgt gaagtccctc tccaacgatg acatcaacaa gatctccggg     660
gacatgaagg acagcctcaa agagatgtcc ctcgaagaga tctactccta cgagaagtac     720
ggggagttca tcacccaaga gggcatcagc ttctacaacg acatctgcgg aaaggtgaac     780
tccttcatga acctctactg ccagaagaac aaagagaaca agaacctgta caagctccag     840
aagctccaca agcagatcct gtgcattgct gacactagct acgaggtgcc atacaagttc     900
gagtccgatg aagaggtgta ccagtccgtg aatggcttcc tcgacaacat ctcctctaag     960
cacatcgtcg agaggcttag gaagatcggc gataactaca acgggtacaa cctggacaag    1020
atctacatcg tgtccaagtt ctacgagtcc gtgagccaga aaacctaccg tgattgggag    1080
actatcaaca ccgctctcga gattcactac aacaacattc tccccggcaa cgggaaatcc    1140
aaggctgata aggttaagaa ggccgtcaag aacgacctcc agaagtctat cactgagatc    1200
aacgagctgg tgtccaacta caagctctgc tccgatgaca catcaaggc cgagacttac    1260 atccacgaga tctcccacat cctgaacaac ttcgaggccc aagagctgaa gtacaaccca    1320
gagattcacc tcgtcgagtc tgagcttaag gcctccgagc ttaagaacgt gctcgacgtt    1380
atcatgaacg ccttccattg gtgctccgtg ttcatgactg aagagttggt ggacaaggat    1440
aacaacttct acgccgagct ggaagaaatc tacgacgaga tctaccccgt gatctccctc    1500
tacaacctcg tgaggaatta cgtgacccag aagccatact ccaccaagaa gatcaagctc    1560
aacttcggga tcccaacctt ggctgatgga tggtccaagt ccaaagagta ctccaacaac    1620
gccatcatcc tgatgaggga caacctgtac tacctcggga tcttcaacgc caagaacaag    1680
cccgacaaga agattatcga ggggaacacc tctgagaaca gggcgacta caaaaagatg    1740 atctacaact gctcccagg gcctaacaag atgatcccca ggtgttcct cagctccaag    1800 actggtgttg agacatacaa gccctccgcc tacattctcg agggatacaa gcaaaacaag    1860
cacatcaagt cctccaagga cttcgatatc accttctgcc acgacctcat cgattatttc    1920
aagaactgca ttgccattca tccagagtgg aagaacttcg gttcgactt ctccgatacc    1980 tccacctacg aggatatctc cggattctac cgtgaggttg agcttcaggg gtacaagatc    2040
gattggacct acatcagcga gaaggacatc gacctgttgc aagagaaggg gcagctttac    2100
ctcttccaaa tctacaacaa agacttctcc aaaaagtcca ccggcaacga caacctccac    2160
```

```
accatgtacc tcaagaacct cttcagcgaa gagaacctca aggacattgt gctcaagctg    2220
aatggcgagg ctgagatttt ctttaggaag tcctctatca agaaccccat catccacaag    2280
aagggctcca tcctcgttaa caggacttac gaggctgaag agaaggacca gttcgggaac    2340
attcagatcg tgcgtaagaa catccccgag aacatctacc aagagcttta caagtacttc    2400
aacgacaagt ccgacaaaga gctgtctgac gaggctgcca agttgaagaa tgtggtggga    2460
catcatgagg ccgctaccaa cattgtgaag gactacaggt acacttacga caagtatttc    2520
ttgcacatgc ccatcaccat caacttcaag gccaacaaga ccggcttcat caacgacagg    2580
atcctccagt acattgccaa agaaaaggac ctccacgtga tcgggattga tagggtgag    2640 cgaaacctca tctacgtgtc agtgatcgat acctgcggga acatcgttga gcagaagtcc    2700
ttcaacatcg ttaacgggta cgactaccag attaagctca agcagcaaga gggtgctaga    2760
cagatcgcta ggaaagagtg gaaagagatc gggaaaatca agagatcaa agaaggctac    2820 ctctccttgg tgattcacga gatcagcaag atggtgatca agtacaacgc tattatcgcc    2880
atggaagatc tcagctacgg cttcaagaag gggcgtttta aggttgagag gcaggtctac    2940
caaaagttcg agactatgct gatcaacaag ctgaactacc tggtgtttaa ggacatctcc    3000
attaccgaga acggcgggct tcttaaggga taccagctca cttacattcc cgacaaactg    3060
aagaacgtgg gtcaccaatg cggctgcatt ttctatgttc agctgcctta cacctccaag    3120
atcgacccaa ctactggatt cgtgaacatc ttcaagttca aggacctcac cgtggacgct    3180
aagagggaat tcatcaagaa gttcgactcc atcaggtacg actccgagaa gaaccttttc    3240
tgcttcacct tcgattacaa caactttatc acccagaaca ccgtgatgtc caagagcagc    3300
tggtcagtgt acacatacgg tgtgaggatc aagcgacgtt tcgtgaacgg aaggttcagc    3360
aacgagagcg atacaatcga catcactaag gacatggaaa agactcttga gatgaccgac    3420
atcaactggc gtgatggtca tgatctcagg caggacatta tcgactacga gatcgtgcag    3480
cacatcttcg aaatcttcag gctcactgtg cagatgagga actcccttag tgagcttgag    3540
gatagggact acgacaggct tatctcccca gtgcttaacg agaacaacat cttctacgac    3600
agcgctaagg ctggggatgc tttgccaaaa gatgctgatg ctaacggggc ttactgtatc    3660
gctttgaagg ggctgtacga gattaagcag atcaccgaga ctggaaaga ggatggcaag    3720 ttctcccgtg acaagctcaa gatctctaac aaggactggt cgatttcat tcagaacaag    3780 cgttacctca gcggcgggtc acctaagaag aagagaaagg tttga                  3825
```

<210> SEQ ID NO 5
<211> LENGTH: 1326
<212> TYPE: PRT
<213> ORGANISM: Artificial Sequence
<220> FEATURE:
<223> OTHER INFORMATION: AsCpf1-NLS

<400> SEQUENCE: 5

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
```

-continued

```
65              70              75              80

Asp Ser Tyr Arg Lys Glu Lys Thr Glu Glu Thr Arg Asn Ala Leu Ile
            85              90              95

Glu Glu Gln Ala Thr Tyr Arg Asn Ala Ile His Asp Tyr Phe Ile Gly
            100             105             110

Arg Thr Asp Asn Leu Thr Asp Ala Ile Asn Lys Arg His Ala Glu Ile
            115             120             125

Tyr Lys Gly Leu Phe Lys Ala Glu Leu Phe Asn Gly Lys Val Leu Lys
        130             135             140

Gln Leu Gly Thr Val Thr Thr Thr Glu His Glu Asn Ala Leu Leu Arg
145             150             155             160

Ser Phe Asp Lys Phe Thr Thr Tyr Phe Ser Gly Phe Tyr Glu Asn Arg
                165             170             175

Lys Asn Val Phe Ser Ala Glu Asp Ile Ser Thr Ala Ile Pro His Arg
            180             185             190

Ile Val Gln Asp Asn Phe Pro Lys Phe Lys Glu Asn Cys His Ile Phe
            195             200             205

Thr Arg Leu Ile Thr Ala Val Pro Ser Leu Arg Glu His Phe Glu Asn
        210             215             220

Val Lys Lys Ala Ile Gly Ile Phe Val Ser Thr Ser Ile Glu Glu Val
225             230             235             240

Phe Ser Phe Pro Phe Tyr Asn Gln Leu Leu Thr Gln Thr Gln Ile Asp
                245             250             255

Leu Tyr Asn Gln Leu Leu Gly Gly Ile Ser Arg Glu Ala Gly Thr Glu
            260             265             270

Lys Ile Lys Gly Leu Asn Glu Val Leu Asn Leu Ala Ile Gln Lys Asn
        275             280             285

Asp Glu Thr Ala His Ile Ile Ala Ser Leu Pro His Arg Phe Ile Pro
        290             295             300

Leu Phe Lys Gln Ile Leu Ser Asp Arg Asn Thr Leu Ser Phe Ile Leu
305             310             315             320

Glu Glu Phe Lys Ser Asp Glu Glu Val Ile Gln Ser Phe Cys Lys Tyr
                325             330             335

Lys Thr Leu Leu Arg Asn Glu Asn Val Leu Glu Thr Ala Glu Ala Leu
            340             345             350

Phe Asn Glu Leu Asn Ser Ile Asp Leu Thr His Ile Phe Ile Ser His
            355             360             365

Lys Lys Leu Glu Thr Ile Ser Ser Ala Leu Cys Asp His Trp Asp Thr
        370             375             380

Leu Arg Asn Ala Leu Tyr Glu Arg Arg Ile Ser Glu Leu Thr Gly Lys
385             390             395             400

Ile Thr Lys Ser Ala Lys Glu Lys Val Gln Arg Ser Leu Lys His Glu
                405             410             415

Asp Ile Asn Leu Gln Glu Ile Ile Ser Ala Ala Gly Lys Glu Leu Ser
            420             425             430

Glu Ala Phe Lys Gln Lys Thr Ser Glu Ile Leu Ser His Ala His Ala
            435             440             445

Ala Leu Asp Gln Pro Leu Pro Thr Thr Leu Lys Lys Gln Glu Glu Lys
        450             455             460

Glu Ile Leu Lys Ser Gln Leu Asp Ser Leu Leu Gly Leu Tyr His Leu
465             470             475             480

Leu Asp Trp Phe Ala Val Asp Glu Ser Asn Glu Val Asp Pro Glu Phe
                485             490             495
```

-continued

```
Ser Ala Arg Leu Thr Gly Ile Lys Leu Glu Met Glu Pro Ser Leu Ser
        500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
        530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
        580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
        610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
        660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
        690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
        740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
        770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
        820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
        850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
        900                 905                 910
```

-continued

```
Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys  Ser Lys Arg Thr Gly  Ile Ala Glu
        995                 1000                1005

Lys Ala  Val Tyr Gln Gln Phe  Glu Lys Met Leu Ile  Asp Lys Leu
    1010                1015                1020

Asn Cys  Leu Val Leu Lys Asp  Tyr Pro Ala Glu Lys  Val Gly Gly
    1025                1030                1035

Val Leu  Asn Pro Tyr Gln Leu  Thr Asp Gln Phe Thr  Ser Phe Ala
    1040                1045                1050

Lys Met  Gly Thr Gln Ser Gly  Phe Leu Phe Tyr Val  Pro Ala Pro
    1055                1060                1065

Tyr Thr  Ser Lys Ile Asp Pro  Leu Thr Gly Phe Val  Asp Pro Phe
    1070                1075                1080

Val Trp  Lys Thr Ile Lys Asn  His Glu Ser Arg Lys  His Phe Leu
    1085                1090                1095

Glu Gly  Phe Asp Phe Leu His  Tyr Asp Val Lys Thr  Gly Asp Phe
    1100                1105                1110

Ile Leu  His Phe Lys Met Asn  Arg Asn Leu Ser Phe  Gln Arg Gly
    1115                1120                1125

Leu Pro  Gly Phe Met Pro Ala  Trp Asp Ile Val Phe  Glu Lys Asn
    1130                1135                1140

Glu Thr  Gln Phe Asp Ala Lys  Gly Thr Pro Phe Ile  Ala Gly Lys
    1145                1150                1155

Arg Ile  Val Pro Val Ile Glu  Asn His Arg Phe Thr  Gly Arg Tyr
    1160                1165                1170

Arg Asp  Leu Tyr Pro Ala Asn  Glu Leu Ile Ala Leu  Leu Glu Glu
    1175                1180                1185

Lys Gly  Ile Val Phe Arg Asp  Gly Ser Asn Ile Leu  Pro Lys Leu
    1190                1195                1200

Leu Glu  Asn Asp Asp Ser His  Ala Ile Asp Thr Met  Val Ala Leu
    1205                1210                1215

Ile Arg  Ser Val Leu Gln Met  Arg Asn Ser Asn Ala  Ala Thr Gly
    1220                1225                1230

Glu Asp  Tyr Ile Asn Ser Pro  Val Arg Asp Leu Asn  Gly Val Cys
    1235                1240                1245

Phe Asp  Ser Arg Phe Gln Asn  Pro Glu Trp Pro Met  Asp Ala Asp
    1250                1255                1260

Ala Asn  Gly Ala Tyr His Ile  Ala Leu Lys Gly Gln  Leu Leu Leu
    1265                1270                1275

Asn His  Leu Lys Glu Ser Lys  Asp Leu Lys Leu Gln  Asn Gly Ile
    1280                1285                1290

Ser Asn  Gln Asp Trp Leu Ala  Tyr Ile Gln Glu Leu  Arg Asn Gly
    1295                1300                1305

Arg Gly  Ser His His His His  His His Lys Leu Pro  Lys Lys Lys
```

-continued

```
          1310            1315            1320

Arg Lys  Val
    1325

<210> SEQ ID NO 6
<211> LENGTH: 3981
<212> TYPE: DNA
<213> ORGANISM: Artificial Sequence
<220> FEATURE:
<223> OTHER INFORMATION: AsCpf1-NLS coding sequence codon optimized for
      S. lycopersicum

<400> SEQUENCE: 6
atgactcagt tcgagggatt cactaacctt taccaggtgt caaagactct taggttcgag      60
cttatcccac agggaaagac tttgaagcac atccaagagc agggattcat cgaagaggat     120
aaggctagga acgatcacta caaagagctt aagccaatca tcgataggat ctacaagact     180
tacgctgatc agtgccttca gcttgtgcag cttgattggg agaacctttc tgctgctatc     240
gattcttata ggaaagaaaa gactgaagag actaggaacg ctcttatcga ggaacaggct     300
acttacagaa acgctatcca cgattacttc atcggaagga ctgataactt gactgatgct     360
atcaacaaga ggcacgctga gatctataag ggacttttca aggctgagct tttcaacgga     420
aaggtgttga agcagcttgg aactgtgact actactgagc acgagaacgc tttgcttaga     480
tctttcgata agttcactac ttacttctct ggattctacg agaacagaaa gaacgtgttc     540
tctgctgagg atatctctac tgctatccca cacaggatcg tgcaggataa cttcccaaag     600
ttcaaagaga actgccacat cttcactagg cttatcactg ctgtgccatc tcttagggaa     660
cacttcgaga acgtgaagaa ggctatcgga atcttcgtgt ctacttcaat cgaggaagtg     720
ttctctttcc ctttctacaa tcaacttctt actcagactc agattgatct ttacaaccag     780
cttcttggag gaatctcaag agaggctgga actgagaaga tcaagggact taacgaggtt     840
ttgaaccttg ctatccaaaa gaacgatgag actgctcaca ttatcgcttc acttccacac     900
agattcatcc ctttgttcaa gcagatcctt tctgatagga acactttgtc tttcatcctt     960
gaagagttca gtctgatga agaggtgatc cagtctttct gcaagtacaa gactcttctt    1020
aggaacgaga atgtgttgga gactgctgag gctctttca atgagcttaa ctctatcgat    1080
cttactcaca ttttcatctc tcacaagaag cttgagacta tctcttctgc tctttgcgat    1140
cactgggata ctttgaggaa cgcactttac gagagaagga tctctgagct tactggaaag    1200
atcactaagt ctgctaaaga aaggttcag agatcactta gcacgagga tatcaacctt    1260 caagagatca tctctgctgc tggaaaagag ctttctgagg ctttcaagca aaagacttct    1320
gagatcttgt ctcacgctca cgctgctctt gatcagccac ttccaactac tcttaagaag    1380
caagaagaga aagagatctt gaagtctcag ttggattctc ttttgggact ttaccacctt    1440
cttgattggt tcgctgtgga tgagtctaac aagtggatc cagagttctc agctaggttg    1500
actggaatca agttggagat ggaaccatct ctttcattct acaacaaggc tagaaactac    1560
gctactaaga agccatactc tgttgagaag ttcaagctta atttccagat gccaactttg    1620
gcttctggat gggatgtgaa caaagaaaaa aacaacggtg ctatccttt cgtgaagaac    1680 ggactttact acttgggaat catgccaaag cagaagggaa ggtacaaggc tttgtcattc    1740
gagccaactg aaaagacatc agagggattc gataagatgt actatgatta cttcccagat    1800
gctgctaaga tgatcccaaa gtgctctact cagcttaagg ctgtgacagc tcacttccag    1860
actcacacta ctccaatcct tttgtctaac aacttcatcg agccacttga tcacaaaaa    1920
```

```
gaaatctacg atcttaacaa ccctgagaaa gagccaaaaa agttccagac tgcttacgct      1980
aaaaagactg gtgatcagaa gggatacagg gaagctttgt gcaagtggat cgatttttact     2040 agggatttct tgtctaagta cactaagact acttctatcg atttgtcatc tttgaggcca      2100
tcttcacagt acaaggatct tggagagtac tacgctgagt tgaacccact tctttaccac      2160
atctcattcc agaggatcgc agagaaagaa atcatggatg ctgttgagac tggaaagctt      2220 tacctttttcc aaatctataa caaggatttc gctaagggac accacggaaa gccaaacctt     2280
cacactcttt actggactgg acttttctca ccagagaact tggctaagac ttctatcaag      2340
ttgaacggac aggctgagtt gttctacagg ccaaagtcta ggatgaagag aatggctcac      2400
aggcttggag agaagatgct taacaaaaag ttgaaggatc aaaagactcc tatcccagat      2460
actctttacc aagagcttta cgattacgtg aaccacaggc tttctcacga tctttctgat      2520
gaggctaggg ctctttttgcc aaacgttatc acaaagagag tgtcacacga gatcatcaag     2580
gatagaaggt ttacttctga taagttcttc ttccacgtgc caatcactct taactaccag      2640
gctgctaact ctccatctaa gttcaaccag agggtgaacg cttaccttaa agagcaccca      2700
gagacaccta tcatcggtat cgatagggga gagaggaacc ttatctacat cactgtgatc      2760
gattctactg gtaagattct tgagcagaga tctttgaaca ctatccagca gttcgattac      2820
cagaagaagt tggataacag ggaaaaagag agggttgcag ctaggcaggc ttggtctgtt      2880
gtgggaacta tcaaggattt gaagcaggga tacttgtctc aggttatcca cgagattgtg      2940
gatttgatga tccactacca agctgtggtg gtgcttgaga accttaactt cggattcaag      3000
tctaagagga ctggtatcgc tgagaaggct gtgtaccaac agttcgagaa gatgttgatc      3060
gataagctta actgccttgt gcttaaggat taccctgctg aaaaggtggg aggtgtgctt      3120
aacccatacc agcttacaga tcagttcact tcattcgcta agatgggaac tcagtctggt      3180
ttcttgttct acgttccagc tccatacaca tcaaagatcg atccattgac tggattcgtg      3240
gatcctttcg tgtggaaaac tattaagaac cacgagtcta ggaagcactt ccttgagggt      3300
ttcgatttcc ttcactacga tgtgaaaact ggtgatttca tcttgcactt taagatgaat      3360
aggaacttgt ctttccagag gggtttgcca ggattcatgc cagcttggga tatcgtgttt      3420
gagaagaacg agacacagtt cgatgctaag ggaactccat tcattgctgg taagaggatt      3480
gtgccagtga ttgagaacca taggttcact ggtaggtaca gggatcttta cccagctaac      3540
gagttgatcg ctttgttgga agagaaggga atcgtgttca gggatggatc taatatcctt      3600
ccaaagcttt tggagaatga tgattctcac gcaatcgata caatggtggc tcttatcaga      3660
tctgtgcttc agatgaggaa ctctaacgct gctactggtg aggattacat caactctcca      3720
gtgagggatc ttaacggtgt gtgcttcgat tctaggttcc agaatcctga gtggccaatg      3780
gatgcagatg ctaacggtgc ttaccacatt gctcttaagg acagcttct tcttaaccac      3840 ttgaaagagt ctaaggatct taagcttcag aacggaatct ctaaccagga ttggcttgct      3900
tacattcaag agcttaggaa tggaagggga tctcatcacc accaccatca caagcttcca      3960
aaaaagaaga ggaaggttta g                                              3981
```

<210> SEQ ID NO 7
<211> LENGTH: 142
<212> TYPE: DNA
<213> ORGANISM: Artificial Sequence
<220> FEATURE:
<223> OTHER INFORMATION: KG10731 (crRNA 1)

-continued

```
<400> SEQUENCE: 7
ggagtgatca aaagtcccac atcgatcagg tgatatatag cagcttagtt tatataatga      60
tagagtcgac atagcgattg tcaaaagacc tttttaattt ctactcttgt agatacttct     120
gaggtttgtg gatcttttt tt                                               142

<210> SEQ ID NO 8
<211> LENGTH: 142
<212> TYPE: DNA
<213> ORGANISM: Artificial Sequence
<220> FEATURE:
<223> OTHER INFORMATION: KG10732 (crRNA 2)

<400> SEQUENCE: 8
ggagtgatca aaagtcccac atcgatcagg tgatatatag cagcttagtt tatataatga      60
tagagtcgac atagcgattg tcaaaagacc tttttaattt ctactcttgt agatagttcc     120
caaagaagac gacctttttt tt                                              142

<210> SEQ ID NO 9
<211> LENGTH: 142
<212> TYPE: DNA
<213> ORGANISM: Artificial Sequence
<220> FEATURE:
<223> OTHER INFORMATION: KG10733 (crRNA 3)

<400> SEQUENCE: 9
ggagtgatca aaagtcccac atcgatcagg tgatatatag cagcttagtt tatataatga      60
tagagtcgac atagcgattg tcaaaagacc tttttaattt ctactcttgt agatatcgtc     120
aggtaataca tcggattttt tt                                              142

<210> SEQ ID NO 10
<211> LENGTH: 142
<212> TYPE: DNA
<213> ORGANISM: Artificial Sequence
<220> FEATURE:
<223> OTHER INFORMATION: KG10734 (crRNA 4)

<400> SEQUENCE: 10
ggagtgatca aaagtcccac atcgatcagg tgatatatag cagcttagtt tatataatga      60
tagagtcgac atagcgattg tcaaaagacc tttttaattt ctactcttgt agatgccata     120
cttgtcgcgg aatactttt tt                                               142

<210> SEQ ID NO 11
<211> LENGTH: 142
<212> TYPE: DNA
<213> ORGANISM: Artificial Sequence
<220> FEATURE:
<223> OTHER INFORMATION: KG10735 (crRNA 5)

<400> SEQUENCE: 11
ggagtgatca aaagtcccac atcgatcagg tgatatatag cagcttagtt tatataatga      60
tagagtcgac atagcgattg tcaaaagacc tttttaattt ctactcttgt agattggacc     120
aagaatgctg caaattttt tt                                               142

<210> SEQ ID NO 12
<211> LENGTH: 142
<212> TYPE: DNA
<213> ORGANISM: Artificial Sequence
<220> FEATURE:
<223> OTHER INFORMATION: KG10736 (crRNA 6)
```

-continued

```
<400> SEQUENCE: 12
ggagtgatca aaagtcccac atcgatcagg tgatatatag cagcttagtt tatataatga        60
tagagtcgac atagcgattg tcaaaagacc tttttaattt ctactcttgt agatatttgc       120
agcattcttg gtccattttt tt                                                142

<210> SEQ ID NO 13
<211> LENGTH: 142
<212> TYPE: DNA
<213> ORGANISM: Artificial Sequence
<220> FEATURE:
<223> OTHER INFORMATION: KG10737 (crRNA 7)

<400> SEQUENCE: 13
ggagtgatca aaagtcccac atcgatcagg tgatatatag cagcttagtt tatataatga        60
tagagtcgac atagcgattg tcaaaagacc tttttaattt ctactcttgt agattccatt       120
ccagtggagt tgatattttt tt                                                142

<210> SEQ ID NO 14
<211> LENGTH: 127
<212> TYPE: DNA
<213> ORGANISM: Artificial Sequence
<220> FEATURE:
<223> OTHER INFORMATION: KG9943 (crRNA 1.1)

<400> SEQUENCE: 14
ggagtgatca aaagtcccac atcgatcagg tgatatatag cagcttagtt tatataatga        60
tagagtcgac atagcgattt aatttctact cttgtagata cttctgaggt ttgtggatct       120
ttttttt                                                                 127

<210> SEQ ID NO 15
<211> LENGTH: 127
<212> TYPE: DNA
<213> ORGANISM: Artificial Sequence
<220> FEATURE:
<223> OTHER INFORMATION: KG9942 (crRNA 2.1)

<400> SEQUENCE: 15
ggagtgatca aaagtcccac atcgatcagg tgatatatag cagcttagtt tatataatga        60
tagagtcgac atagcgattt aatttctact cttgtagata gttcccaaag aagacgacct       120
ttttttt                                                                 127

<210> SEQ ID NO 16
<211> LENGTH: 127
<212> TYPE: DNA
<213> ORGANISM: Artificial Sequence
<220> FEATURE:
<223> OTHER INFORMATION: KG10533 (crRNA 3.1)

<400> SEQUENCE: 16
ggagtgatca aaagtcccac atcgatcagg tgatatatag cagcttagtt tatataatga        60
tagagtcgac atagcgattt aatttctact cttgtagata tcgtcaggta atacatcgga       120
ttttttt                                                                 127

<210> SEQ ID NO 17
<211> LENGTH: 127
<212> TYPE: DNA
<213> ORGANISM: Artificial Sequence
<220> FEATURE:
```

```
<223> OTHER INFORMATION: KG10106 (crRNA 4.1)

<400> SEQUENCE: 17
ggagtgatca aaagtcccac atcgatcagg tgatatatag cagcttagtt tatataatga      60
tagagtcgac atagcgattt aatttctact cttgtagatg ccatacttgt cgcggaatac     120
ttttttt                                                               127

<210> SEQ ID NO 18
<211> LENGTH: 127
<212> TYPE: DNA
<213> ORGANISM: Artificial Sequence
<220> FEATURE:
<223> OTHER INFORMATION: KG10101 (crRNA 5.1)

<400> SEQUENCE: 18
ggagtgatca aaagtcccac atcgatcagg tgatatatag cagcttagtt tatataatga      60
tagagtcgac atagcgattt aatttctact cttgtagatt ggaccaagaa tgctgcaaat     120
ttttttt                                                               127

<210> SEQ ID NO 19
<211> LENGTH: 127
<212> TYPE: DNA
<213> ORGANISM: Artificial Sequence
<220> FEATURE:
<223> OTHER INFORMATION: KG10102 (crRNA 6.1)

<400> SEQUENCE: 19
ggagtgatca aaagtcccac atcgatcagg tgatatatag cagcttagtt tatataatga      60
tagagtcgac atagcgattt aatttctact cttgtagata tttgcagcat tcttggtcca     120
ttttttt                                                               127

<210> SEQ ID NO 20
<211> LENGTH: 127
<212> TYPE: DNA
<213> ORGANISM: Artificial Sequence
<220> FEATURE:
<223> OTHER INFORMATION: KG10104 (crRNA 7.1)

<400> SEQUENCE: 20
ggagtgatca aaagtcccac atcgatcagg tgatatatag cagcttagtt tatataatga      60
tagagtcgac atagcgattt aatttctact cttgtagatt ccattccagt ggagttgata     120
ttttttt                                                               127

<210> SEQ ID NO 21
<211> LENGTH: 38
<212> TYPE: DNA
<213> ORGANISM: Artificial Sequence
<220> FEATURE:
<223> OTHER INFORMATION: scaffold

<400> SEQUENCE: 21
ccgtctaaaa ctcattcaga atttctacta gtgtagat                              38

<210> SEQ ID NO 22
<211> LENGTH: 36
<212> TYPE: DNA
<213> ORGANISM: Artificial Sequence
<220> FEATURE:
<223> OTHER INFORMATION: scaffold

<400> SEQUENCE: 22
```

```
ctctacaact gataaagaat ttctactttt gtagat                                   36

<210> SEQ ID NO 23
<211> LENGTH: 36
<212> TYPE: DNA
<213> ORGANISM: Artificial Sequence
<220> FEATURE:
<223> OTHER INFORMATION: scaffold

<400> SEQUENCE: 23
gtctggcccc aaattttaat ttctactgtt gtagat                                   36

<210> SEQ ID NO 24
<211> LENGTH: 35
<212> TYPE: DNA
<213> ORGANISM: Artificial Sequence
<220> FEATURE:
<223> OTHER INFORMATION: scaffold

<400> SEQUENCE: 24
gtcaaaagac ctttttaatt tctactcttg tagat                                    35

<210> SEQ ID NO 25
<211> LENGTH: 684
<212> TYPE: DNA
<213> ORGANISM: Artificial Sequence
<220> FEATURE:
<223> OTHER INFORMATION: rAPOBEC1 encoding sequence

<400> SEQUENCE: 25
atgagcagcg aaaccggtcc ggttgcagtt gatccgaccc tgcgtcgtcg tattgaaccg          60
catgaatttg aagttttttt tgatccgcgt gaactgcgta agaaacctg tctgctgtat          120 gaaattaatt ggggtggtcg tcatagcatt tggcgtcata ccagccagaa taccaataaa         180
catgttgaag ttaattttat tgaaaaattt accaccgaac gttatttttg tccgaatacc         240
cgttgtagca ttacctggtt tctgagctgg agcccgtgtg gtgaatgtag ccgtgcaatt         300
accgaatttc tgagccgtta tccgcatgtt accctgttta tttatattgc acgtctgtat         360
catcatgcag atccgcgtaa tcgtcagggt ctgcgtgatc tgattagcag cggtgttacc         420
attcagatta tgaccgaaca ggaaagcggt tattgttggc gtaattttgt taattatagc         480
ccgagcaatg aagcacattg gccgcgttat ccgcatctgt gggttcgtct gtatgttctg         540
gaactgtatt gtattattct gggtctgccg ccgtgtctga atattctgcg tcgtaaacag         600
ccgcagctga cctttttttac cattgcactg cagagctgtc attatcagcg tctgccgccg         660
catattctgt gggcaaccgg tctg                                                684

<210> SEQ ID NO 26
<211> LENGTH: 228
<212> TYPE: PRT
<213> ORGANISM: Artificial Sequence
<220> FEATURE:
<223> OTHER INFORMATION: rAPOBEC1

<400> SEQUENCE: 26

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
            20                  25                  30

Arg Lys Glu Thr Cys Leu Leu Tyr Glu Ile Asn Trp Gly Gly Arg His
        35                  40                  45
```

-continued

```
Ser Ile Trp Arg His Thr Ser Gln Asn Thr Asn Lys His Val Glu Val
    50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
                100                 105                 110

Phe Ile Tyr Ile Ala Arg Leu Tyr His His Ala Asp Pro Arg Asn Arg
            115                 120                 125

Gln Gly Leu Arg Asp Leu Ile Ser Ser Gly Val Thr Ile Gln Ile Met
    130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
                180                 185                 190

Leu Asn Ile Leu Arg Arg Lys Gln Pro Gln Leu Thr Phe Phe Thr Ile
            195                 200                 205

Ala Leu Gln Ser Cys His Tyr Gln Arg Leu Pro Pro His Ile Leu Trp
    210                 215                 220

Ala Thr Gly Leu
225

<210> SEQ ID NO 27
<211> LENGTH: 501
<212> TYPE: DNA
<213> ORGANISM: Artificial Sequence
<220> FEATURE:
<223> OTHER INFORMATION: TadA encoding sequence

<400> SEQUENCE: 27
atgtccgagg tcgagttctc tcatgagtac tggatgaggc acgctctcac tcttgctaaa      60
agagcttggg acgagagaga ggttccagtt ggagctgttt tggtgcacaa caaccgtgtg     120
attggcgaag gatggaacag gccaattgga aggcatgatc caactgctca cgctgagatt     180
atggccctta gacaaggtgg actcgtgatg cagaactaca ggcttatcga cgccactctc     240
tacgtgacac ttgagccatg tgttatgtgc gctggtgcca tgattcactc caggattgga     300
agggttgtgt cggagctag agatgctaaa actggcgctg ccggatctct catggatgtg     360
cttcatcatc ctgggatgaa ccacagggtt gagatcactg agggaatcct tgctgatgag     420
tgcgctgctc tcctgtctga ttttttcagg atgaggcgtc aagagatcaa ggcccagaag     480
aaggctcagt cctctactga t                                              501

<210> SEQ ID NO 28
<211> LENGTH: 167
<212> TYPE: PRT
<213> ORGANISM: Artificial Sequence
<220> FEATURE:
<223> OTHER INFORMATION: TadA

<400> SEQUENCE: 28

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
```

-continued

```
                20              25              30

Val Leu Val His Asn Asn Arg Val Ile Gly Glu Gly Trp Asn Arg Pro
        35              40              45

Ile Gly Arg His Asp Pro Thr Ala His Ala Glu Ile Met Ala Leu Arg
    50              55              60

Gln Gly Gly Leu Val Met Gln Asn Tyr Arg Leu Ile Asp Ala Thr Leu
65              70              75              80

Tyr Val Thr Leu Glu Pro Cys Val Met Cys Ala Gly Ala Met Ile His
            85              90              95

Ser Arg Ile Gly Arg Val Val Phe Gly Ala Arg Asp Ala Lys Thr Gly
            100             105             110

Ala Ala Gly Ser Leu Met Asp Val Leu His His Pro Gly Met Asn His
        115             120             125

Arg Val Glu Ile Thr Glu Gly Ile Leu Ala Asp Glu Cys Ala Ala Leu
    130             135             140

Leu Ser Asp Phe Phe Arg Met Arg Arg Gln Glu Ile Lys Ala Gln Lys
145             150             155             160

Lys Ala Gln Ser Ser Thr Asp
            165
```

```
<210> SEQ ID NO 29
<211> LENGTH: 5
<212> TYPE: PRT
<213> ORGANISM: Artificial Sequence
<220> FEATURE:
<223> OTHER INFORMATION: linker

<400> SEQUENCE: 29

Glu Ala Ala Ala Lys
1               5
```

```
<210> SEQ ID NO 30
<211> LENGTH: 11
<212> TYPE: PRT
<213> ORGANISM: Artificial Sequence
<220> FEATURE:
<223> OTHER INFORMATION: linker

<400> SEQUENCE: 30

Ser Pro Lys Lys Lys Arg Lys Val Glu Ala Ser
1               5               10
```

```
<210> SEQ ID NO 31
<211> LENGTH: 16
<212> TYPE: PRT
<213> ORGANISM: Artificial Sequence
<220> FEATURE:
<223> OTHER INFORMATION: linker

<400> SEQUENCE: 31

Ser Gly Ser Glu Thr Pro Gly Thr Ser Glu Ser Ala Thr Pro Glu Ser
1               5               10              15
```

```
<210> SEQ ID NO 32
<211> LENGTH: 17
<212> TYPE: PRT
<213> ORGANISM: Artificial Sequence
<220> FEATURE:
<223> OTHER INFORMATION: linker

<400> SEQUENCE: 32

Lys Ser Gly Ser Glu Thr Pro Gly Thr Ser Glu Ser Ala Thr Pro Glu
```

```
1               5              10             15

Ser

<210> SEQ ID NO 33
<211> LENGTH: 252
<212> TYPE: DNA
<213> ORGANISM: Artificial Sequence
<220> FEATURE:
<223> OTHER INFORMATION: UGI encoding sequence

<400> SEQUENCE: 33
atgactaatc tgtcagatat tattgaaaag gagaccggta agcaactggt tatccaggaa      60
tccatcctca tgctcccaga ggaggtggaa gaagtcattg ggaacaagcc ggaaagcgat     120
atactcgtgc acaccgccta cgacgagagc accgacgaga atgtcatgct tctgactagc     180 gacgccctg aatacaagcc ttgggctctg gtcatacagg atagcaacgg tgagaacaag      240
attaagatgc tc                                                        252

<210> SEQ ID NO 34
<211> LENGTH: 84
<212> TYPE: PRT
<213> ORGANISM: Artificial Sequence
<220> FEATURE:
<223> OTHER INFORMATION: UGI

<400> SEQUENCE: 34

Met Thr Asn Leu Ser Asp Ile Ile Glu Lys Glu Thr Gly Lys Gln Leu
1               5                  10                  15

Val Ile Gln Glu Ser Ile Leu Met Leu Pro Glu Glu Val Glu Glu Val
            20                  25                  30

Ile Gly Asn Lys Pro Glu Ser Asp Ile Leu Val His Thr Ala Tyr Asp
        35                  40                  45

Glu Ser Thr Asp Glu Asn Val Met Leu Leu Thr Ser Asp Ala Pro Glu
    50                  55                  60

Tyr Lys Pro Trp Ala Leu Val Ile Gln Asp Ser Asn Gly Glu Asn Lys
65                  70                  75                  80

Ile Lys Met Leu

<210> SEQ ID NO 35
<211> LENGTH: 168
<212> TYPE: DNA
<213> ORGANISM: Artificial Sequence
<220> FEATURE:
<223> OTHER INFORMATION: UGI encoding sequence

<400> SEQUENCE: 35
accaatctga gcgatatcat tgaaaaagaa accggcaaac agctggtgat tcaagaaagc      60
attctgatgc tgcctgaaga agtggaagaa gttattggta ataaaccgga aagcgatatt     120
ctggttcata ccgcatatga tgaaagcacc gatgaaaatg ttatgctg                 168

<210> SEQ ID NO 36
<211> LENGTH: 56
<212> TYPE: PRT
<213> ORGANISM: Artificial Sequence
<220> FEATURE:
<223> OTHER INFORMATION: UGI

<400> SEQUENCE: 36

Thr Asn Leu Ser Asp Ile Ile Glu Lys Glu Thr Gly Lys Gln Leu Val
1               5                  10                  15
```

-continued

```
Ile Gln Glu Ser Ile Leu Met Leu Pro Glu Glu Val Glu Glu Val Ile
        20                  25                  30

Gly Asn Lys Pro Glu Ser Asp Ile Leu Val His Thr Ala Tyr Asp Glu
        35                  40                  45

Ser Thr Asp Glu Asn Val Met Leu
    50                  55
```

<210> SEQ ID NO 37
<211> LENGTH: 681
<212> TYPE: DNA
<213> ORGANISM: Artificial Sequence
<220> FEATURE:
<223> OTHER INFORMATION: rAPOBEC1 encoding sequence

<400> SEQUENCE: 37

```
atgagcagcg aaacaggtcc ggttgcagtt gatccgaccc tgcgtcgtcg tattgaaccg      60
catgaatttg aagttttttt tgatccgcgt gagctgcgta aagaaacctg tctgctgtat     120
gaaattaact ggggtggtcg tcatagcatt tggcgtcata ccagccagaa taccaataaa     180
catgtggaag tgaacttcat cgagaaattt accaccgaac gttattttg tccgaatacc      240 cgttgtagca ttacctggtt tctgagctgg tcaccgtgtg gtgaatgtag ccgtgcaatt     300
accgaatttc tgagccgtta tccgcatgtt accctgttta tctatattgc ccgtctgtat     360
catcatgcag atccgcgtaa tcgtcagggt ctgcgtgatc tgattagcag cggtgttacc     420
attcagatta tgaccgaaca agaaagcggt tattgctggc gtaattttgt gaattatagc     480
ccgagcaatg aagcacattg ccctcgctat ccgcatctgt gggttcgtct gtatgttctg     540
gaactgtatt gtattattct gggtctgcct ccgtgtctga atattctgcg tcgtaaacag     600
ccgcagctga ccttttttac cattgcactg cagagctgtc attatcagcg tctgccaccg     660
catattctgt gggcaacagg t                                               681
```

<210> SEQ ID NO 38
<211> LENGTH: 31
<212> TYPE: DNA
<213> ORGANISM: Lycopersicon esculentum

<400> SEQUENCE: 38

```
cgtttaactt ctgaggtttg tggatctttt a                                     31
```

<210> SEQ ID NO 39
<211> LENGTH: 35
<212> TYPE: DNA
<213> ORGANISM: Lycopersicon esculentum

<400> SEQUENCE: 39

```
actttcagtt cccaaagaag acgacctcga gctcc                                 35
```

<210> SEQ ID NO 40
<211> LENGTH: 31
<212> TYPE: DNA
<213> ORGANISM: Lycopersicon esculentum

<400> SEQUENCE: 40

```
aatttcatcg tcaggtaata catcggattc a                                     31
```

<210> SEQ ID NO 41
<211> LENGTH: 31
<212> TYPE: DNA
<213> ORGANISM: Lycopersicon esculentum

<400> SEQUENCE: 41
ggtttagcca tacttgtcgc ggaatacctt g                                31

<210> SEQ ID NO 42
<211> LENGTH: 30
<212> TYPE: DNA
<213> ORGANISM: Lycopersicon esculentum

<400> SEQUENCE: 42
gctttgtgga ccaagaatgc tgcaaatgaa                                  30

<210> SEQ ID NO 43
<211> LENGTH: 29
<212> TYPE: DNA
<213> ORGANISM: Lycopersicon esculentum

<400> SEQUENCE: 43
tgtttcattt gcagcattct tggtccaca                                   29

<210> SEQ ID NO 44
<211> LENGTH: 31
<212> TYPE: DNA
<213> ORGANISM: Lycopersicon esculentum

<400> SEQUENCE: 44
tatttctcca ttccagtgga gttgatatac t                                31

<210> SEQ ID NO 45
<211> LENGTH: 21
<212> TYPE: DNA
<213> ORGANISM: Artificial Sequence
<220> FEATURE:
<223> OTHER INFORMATION: mutant

<400> SEQUENCE: 45
cgtttaactt ctgaggtttt a                                           21

<210> SEQ ID NO 46
<211> LENGTH: 22
<212> TYPE: DNA
<213> ORGANISM: Artificial Sequence
<220> FEATURE:
<223> OTHER INFORMATION: mutant

<400> SEQUENCE: 46
cgtttaactt ctgaggtttg ta                                          22

<210> SEQ ID NO 47
<211> LENGTH: 21
<212> TYPE: DNA
<213> ORGANISM: Artificial Sequence
<220> FEATURE:
<223> OTHER INFORMATION: mutant

<400> SEQUENCE: 47
cgtttaactt ctgaggtttt a                                           21

<210> SEQ ID NO 48
<211> LENGTH: 22
<212> TYPE: DNA
<213> ORGANISM: Artificial Sequence
<220> FEATURE:
<223> OTHER INFORMATION: mutant -continued

```
<400> SEQUENCE: 48
cgtttaactt ctgaggtttt ta                                          22

<210> SEQ ID NO 49
<211> LENGTH: 29
<212> TYPE: DNA
<213> ORGANISM: Artificial Sequence
<220> FEATURE:
<223> OTHER INFORMATION: mutant

<400> SEQUENCE: 49
actttcagtt cccaaagaag acgagctcc                                   29

<210> SEQ ID NO 50
<211> LENGTH: 32
<212> TYPE: DNA
<213> ORGANISM: Artificial Sequence
<220> FEATURE:
<223> OTHER INFORMATION: mutant

<400> SEQUENCE: 50
actttcagtt cccaaagaag acctcgagct cc                               32

<210> SEQ ID NO 51
<211> LENGTH: 29
<212> TYPE: DNA
<213> ORGANISM: Artificial Sequence
<220> FEATURE:
<223> OTHER INFORMATION: mutant

<400> SEQUENCE: 51
actttcagtt cccaaagaag acgagctcc                                   29

<210> SEQ ID NO 52
<211> LENGTH: 26
<212> TYPE: DNA
<213> ORGANISM: Artificial Sequence
<220> FEATURE:
<223> OTHER INFORMATION: mutant

<400> SEQUENCE: 52
actttcagtt cccaaagaag agctcc                                      26

<210> SEQ ID NO 53
<211> LENGTH: 23
<212> TYPE: DNA
<213> ORGANISM: Artificial Sequence
<220> FEATURE:
<223> OTHER INFORMATION: mutant

<400> SEQUENCE: 53
aatttcatcg tcaggtaata tca                                         23

<210> SEQ ID NO 54
<211> LENGTH: 26
<212> TYPE: DNA
<213> ORGANISM: Artificial Sequence
<220> FEATURE:
<223> OTHER INFORMATION: mutant

<400> SEQUENCE: 54
aatttcatcg tcaggtaata cattca                                      26

<210> SEQ ID NO 55
<211> LENGTH: 23
```

-continued

```
<212> TYPE: DNA
<213> ORGANISM: Artificial Sequence
<220> FEATURE:
<223> OTHER INFORMATION: mutant

<400> SEQUENCE: 55
aatttcatcg tcaggtaata cca                                           23

<210> SEQ ID NO 56
<211> LENGTH: 26
<212> TYPE: DNA
<213> ORGANISM: Artificial Sequence
<220> FEATURE:
<223> OTHER INFORMATION: mutant

<400> SEQUENCE: 56
aatttcatcg tcaggtaata gattca                                        26

<210> SEQ ID NO 57
<211> LENGTH: 23
<212> TYPE: DNA
<213> ORGANISM: Artificial Sequence
<220> FEATURE:
<223> OTHER INFORMATION: mutant

<400> SEQUENCE: 57
ggtttagcca tacttgtcgc ttg                                           23

<210> SEQ ID NO 58
<211> LENGTH: 22
<212> TYPE: DNA
<213> ORGANISM: Artificial Sequence
<220> FEATURE:
<223> OTHER INFORMATION: mutant

<400> SEQUENCE: 58
ggtttagcca tacttgtcgc tg                                            22

<210> SEQ ID NO 59
<211> LENGTH: 22
<212> TYPE: DNA
<213> ORGANISM: Artificial Sequence
<220> FEATURE:
<223> OTHER INFORMATION: mutant

<400> SEQUENCE: 59
ggtttagcca tacttgtcgc tg                                            22

<210> SEQ ID NO 60
<211> LENGTH: 21
<212> TYPE: DNA
<213> ORGANISM: Artificial Sequence
<220> FEATURE:
<223> OTHER INFORMATION: mutant

<400> SEQUENCE: 60
ggtttagcca tacttgtcgc g                                             21

<210> SEQ ID NO 61
<211> LENGTH: 21
<212> TYPE: DNA
<213> ORGANISM: Artificial Sequence
<220> FEATURE:
<223> OTHER INFORMATION: mutant

<400> SEQUENCE: 61
```

-continued

```
gctttgtgga ccaagaatga a                                      21

<210> SEQ ID NO 62
<211> LENGTH: 24
<212> TYPE: DNA
<213> ORGANISM: Artificial Sequence
<220> FEATURE:
<223> OTHER INFORMATION: mutant

<400> SEQUENCE: 62
gctttgtgga ccaagaatgc tgaa                                   24

<210> SEQ ID NO 63
<211> LENGTH: 18
<212> TYPE: DNA
<213> ORGANISM: Artificial Sequence
<220> FEATURE:
<223> OTHER INFORMATION: mutant

<400> SEQUENCE: 63
gctttgtgga ccaagaaa                                          18

<210> SEQ ID NO 64
<211> LENGTH: 24
<212> TYPE: DNA
<213> ORGANISM: Artificial Sequence
<220> FEATURE:
<223> OTHER INFORMATION: mutant

<400> SEQUENCE: 64
gctttgtgga ccaagaatgc tgaa                                   24

<210> SEQ ID NO 65
<211> LENGTH: 20
<212> TYPE: DNA
<213> ORGANISM: Artificial Sequence
<220> FEATURE:
<223> OTHER INFORMATION: mutant

<400> SEQUENCE: 65
tgtttcattt gcagcattca                                        20

<210> SEQ ID NO 66
<211> LENGTH: 19
<212> TYPE: DNA
<213> ORGANISM: Artificial Sequence
<220> FEATURE:
<223> OTHER INFORMATION: mutant

<400> SEQUENCE: 66
tgtttcattt gcagcattc                                         19

<210> SEQ ID NO 67
<211> LENGTH: 22
<212> TYPE: DNA
<213> ORGANISM: Artificial Sequence
<220> FEATURE:
<223> OTHER INFORMATION: mutant

<400> SEQUENCE: 67
tgtttcattt gcagcattct ta                                     22

<210> SEQ ID NO 68
<211> LENGTH: 20
<212> TYPE: DNA
<213> ORGANISM: Artificial Sequence
```

-continued

```
<220> FEATURE:
<223> OTHER INFORMATION: mutant

<400> SEQUENCE: 68
tgtttcattt gcagcattct                                              20

<210> SEQ ID NO 69
<211> LENGTH: 26
<212> TYPE: DNA
<213> ORGANISM: Artificial Sequence
<220> FEATURE:
<223> OTHER INFORMATION: mutant

<400> SEQUENCE: 69
tatttctcca ttccagtgga gttact                                       26

<210> SEQ ID NO 70
<211> LENGTH: 24
<212> TYPE: DNA
<213> ORGANISM: Artificial Sequence
<220> FEATURE:
<223> OTHER INFORMATION: mutant

<400> SEQUENCE: 70
tatttctcca ttccagtgga tact                                         24

<210> SEQ ID NO 71
<211> LENGTH: 24
<212> TYPE: DNA
<213> ORGANISM: Artificial Sequence
<220> FEATURE:
<223> OTHER INFORMATION: mutant

<400> SEQUENCE: 71
tatttctcca ttccagtgga tact                                         24

<210> SEQ ID NO 72
<211> LENGTH: 22
<212> TYPE: DNA
<213> ORGANISM: Artificial Sequence
<220> FEATURE:
<223> OTHER INFORMATION: mutant

<400> SEQUENCE: 72
tatttctcca ttccagtgga ct                                           22

<210> SEQ ID NO 73
<211> LENGTH: 35
<212> TYPE: DNA
<213> ORGANISM: artificial sequence
<220> FEATURE:
<223> OTHER INFORMATION: scaffold

<400> SEQUENCE: 73
gttaagttat atagaataat ttctactgtt gtaga                             35

<210> SEQ ID NO 74
<211> LENGTH: 3792
<212> TYPE: DNA
<213> ORGANISM: artificial sequence
<220> FEATURE:
<223> OTHER INFORMATION: MAD7 coding sequence codon optimized for S.
      lycopersicum

<400> SEQUENCE: 74
atgaacaacg ggaccaacaa cttccagaac ttcatcggga tcagctccct ccaaaagacc    60
```

-continued

```
cttaggaacg ctcttatccc aaccgagact acccagcagt tcatcgtgaa gaacgggatc      120
atcaaagagg acgagcttag gggagagaac aggcagatcc tcaaggatat catggacgac      180
tactacaggg gcttcatctc cgagactctg tcctccatcg atgatatcga ctggacctcc      240
ttgttcgaga agatggaaat ccagctcaag aacggggaca acaaggacac ccttatcaaa      300
gagcagaccg agtaccgtaa ggccatccac aaaaagttcg ctaacgacga caggttcaag      360
aatatgttct ccgccaagct catcagcgac atccttccag agttcgtgat ccacaacaac      420
aactactccg cctccgagaa agaggaaaag acccaggtca tcaagctgtt ctccaggttc      480
gctacctcct tcaaggacta cttcaagaac agggccaact gcttctccgc cgacgatatc      540
tcttcatctt cttgccacag gatcgtgaac gacaacgccg agatcttctt ctccaacgct      600
cttgtgtaca ggcgtatcgt gaagtccctc tccaacgatg acatcaacaa gatctccggg      660
gacatgaagg acagcctcaa agagatgtcc ctcgaagaga tctactccta cgagaagtac      720
ggggagttca tcacccaaga gggcatcagc ttctacaacg acatctgcgg aaaggtgaac      780
tccttcatga acctctactg ccagaagaac aaagagaaca agaacctgta caagctccag      840
aagctccaca agcagatcct gtgcattgct gacactagct acgaggtgcc atacaagttc      900
gagtccgatg aagaggtgta ccagtccgtg aatggcttcc tcgacaacat ctcctctaag      960
cacatcgtcg agaggcttag gaagatcggc gataactaca acgggtacaa cctggacaag     1020
atctacatcg tgtccaagtt ctacgagtcc gtgagccaga aaacctaccg tgattgggag     1080
actatcaaca ccgctctcga gattcactac aacaacattc tccccggcaa cgggaaatcc     1140
aaggctgata aggttaagaa ggccgtcaag aacgacctcc agaagtctat cactgagatc     1200
aacgagctgg tgtccaacta caagctctgc tccgatgaca acatcaaggc cgagacttac     1260
atccacgaga tctcccacat cctgaacaac ttcgaggccc aagagctgaa gtacaaccca     1320
gagattcacc tcgtcgagtc tgagcttaag gcctccgagc ttaagaacgt gctcgacgtt     1380
atcatgaacg ccttccattg gtgctccgtg ttcatgactg aagagttggt ggacaaggat     1440
aacaacttct acgccgagct ggaagaaatc tacgacgaga tctacccccgt gatctccctc     1500 tacaacctcg tgaggaatta cgtgacccag aagccatact ccaccaagaa gatcaagctc     1560
aacttcggga tcccaacctt ggctgatgga tggtccaagt ccaaagagta ctccaacaac     1620
gccatcatcc tgatgaggga caacctgtac tacctcggga tcttcaacgc caagaacaag     1680
cccgacaaga agattatcga ggggaacacc tctgagaaca agggcgacta caaaaagatg     1740
atctacaact tgctccccagg gcctaacaag atgatcccca aggtgttcct cagctccaag     1800
actggtgttg agacatacaa gcccctccgcc tacattctcg agggatacaa gcaaaacaag     1860
cacatcaagt cctccaagga cttcgatatc accttctgcc acgacctcat cgattatttc     1920
aagaactgca ttgccattca tccagagtgg aagaacttcg ggttcgactt ctccgatacc     1980
tccacctacg aggatatctc cggattctac cgtgaggttg agcttcaggg gtacaagatc     2040
gattggacct acatcagcga gaaggacatc gacctgttgc aagagaaggg gcagctttac     2100
ctcttccaaa tctacaacaa agacttctcc aaaaagtcca ccggcaacga caacctccac     2160
accatgtacc tcaagaacct cttcagcgaa gagaacctcc aggacattgt gctcaagctg     2220
aatggcgagg ctgagatttt ctttaggaag tcctctatca agaaccccat catccacaag     2280
aagggctcca tcctcgttaa caggacttac gaggctgaag agaaggacca gttcgggaac     2340
attcagatcg tgcgtaagaa catccccgag aacatctacc aagagcttta caagtacttc     2400
```

-continued

```
aacgacaagt ccgacaaaga gctgtctgac gaggctgcca agttgaagaa tgtggtggga      2460
catcatgagg ccgctaccaa cattgtgaag gactacaggt acacttacga caagtatttc      2520
ttgcacatgc ccatcaccat caacttcaag gccaacaaga ccggcttcat caacgacagg      2580
atcctccagt acattgccaa agaaaaggac ctccacgtga tcgggattga taggggtgag      2640
cgaaacctca tctacgtgtc agtgatcgat acctgcggga acatcgttga gcagaagtcc      2700
ttcaacatcg ttaacgggta cgactaccag attaagctca agcagcaaga gggtgctaga      2760
cagatcgcta ggaaagagtg gaaagagatc gggaaaatca aagagatcaa agaaggctac      2820
ctctccttgg tgattcacga gatcagcaag atggtgatca gtacaacgc tattatcgcc      2880 atggaagatc tcagctacgg cttcaagaag gggcgtttta aggttgagag gcaggtctac      2940
caaaagttcg agactatgct gatcaacaag ctgaactacc tggtgtttaa ggacatctcc      3000
attaccgaga acggcgggct tcttaaggga taccagctca cttacattcc cgacaaactg      3060
aagaacgtgg gtcaccaatg cggctgcatt ttctatgttc cagctgccta cacctccaag      3120
atcgacccaa ctactggatt cgtgaacatc ttcaagttca aggacctcac cgtggacgct      3180
aagagggaat tcatcaagaa gttcgactcc atcaggtacg actccgagaa gaaccttttc      3240
tgcttcacct tcgattacaa caactttatc acccagaaca ccgtgatgtc caagagcagc      3300
tggtcagtgt acacatacgg tgtgaggatc aagcgacgtt tcgtgaacgg aaggttcagc      3360
aacgagagcg atacaatcga catcactaag gacatggaaa agactcttga gatgaccgac      3420
atcaactggc gtgatggtca tgatctcagg caggacatta tcgactacga gatcgtgcag      3480
cacatcttcg aaatcttcag gctcactgtg cagatgagga actcccttag tgagcttgag      3540
gatagggact acgacaggct tatctcccca gtgcttaacg agaacaacat cttctacgac      3600
agcgctaagc tgggggatgc tttgccaaaa gatgctgatg ctaacggggc ttactgtatc      3660
gctttgaagg ggctgtacga gattaagcag atcaccgaga actggaaaga ggatggcaag      3720
ttctcccgtg acaagctcaa gatctctaac aaggactggt cgatttcat tcagaacaag      3780 cgttacctct ga                                                         3792
```

<210> SEQ ID NO 75
<211> LENGTH: 35
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(35)
<223> OTHER INFORMATION: This sequence may encompass 1-7 "Gly Gly Gly
      Gly Ser" repeating units

<400> SEQUENCE: 75

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35
```

<210> SEQ ID NO 76
<211> LENGTH: 21
<212> TYPE: PRT
<213> ORGANISM: Artificial Sequence
<220> FEATURE:
<223> OTHER INFORMATION: Synthetic peptide -continued

```
<220> FEATURE:
<221> NAME/KEY: MISC_FEATURE
<222> LOCATION: (1)..(21)
<223> OTHER INFORMATION: This sequence may encompass 1-7 "Gly Gly Ser"
      repeating units

<400> SEQUENCE: 76

Gly Gly Ser Gly Gly Ser Gly Gly Ser Gly Gly Ser Gly Gly Ser Gly
1               5                   10                  15

Gly Ser Gly Gly Ser
            20

<210> SEQ ID NO 77
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(7)
<223> OTHER INFORMATION: This sequence may encompass 1-7 "Gly" repeating
      units

<400> SEQUENCE: 77

Gly Gly Gly Gly Gly Gly Gly
1               5
```